United States Patent
Khatib

(10) Patent No.: US 10,323,284 B2
(45) Date of Patent: Jun. 18, 2019

(54) SINGLE NUCLEOTIDE POLYMORPHISMS ASSOCIATED WITH BULL FERTILITY

(71) Applicant: WISCONSIN ALUMNI RESEARCH FOUNDATION, Madison, WI (US)

(72) Inventor: Hasan Khatib, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 144 days.

(21) Appl. No.: 15/688,901

(22) Filed: Aug. 29, 2017

(65) Prior Publication Data

US 2018/0002755 A1 Jan. 4, 2018

Related U.S. Application Data

(62) Division of application No. 14/754,729, filed on Jun. 30, 2015, now Pat. No. 9,777,331, which is a division of application No. 13/798,181, filed on Mar. 13, 2013, now Pat. No. 9,102,985.

(60) Provisional application No. 61/681,152, filed on Aug. 9, 2012.

(51) Int. Cl.
| | | |
|---|---|---|
| C12Q 1/68 | (2018.01) | |
| C12Q 1/6883 | (2018.01) | |
| C12Q 1/6888 | (2018.01) | |
| A01K 67/02 | (2006.01) | |
| A01K 67/027 | (2006.01) | |
| A61D 19/04 | (2006.01) | |
| A61K 35/54 | (2015.01) | |

(52) U.S. Cl.
CPC ............ *C12Q 1/6883* (2013.01); *A01K 67/02* (2013.01); *A01K 67/027* (2013.01); *A61D 19/04* (2013.01); *A61K 35/54* (2013.01); *C12Q 1/68* (2013.01); *C12Q 1/6888* (2013.01); *A01K 2227/101* (2013.01); *A01K 2267/02* (2013.01); *C12Q 2600/124* (2013.01); *C12Q 2600/156* (2013.01); *C12Q 2600/16* (2013.01)

(58) Field of Classification Search
None
See application file for complete search history.

(56) References Cited

PUBLICATIONS

Barendse et al. Mammalian Genome 8, 21-28 (1997) (Year: 1997).*

* cited by examiner

*Primary Examiner* — Juliet C Switzer
(74) *Attorney, Agent, or Firm* — Kening Li; Duane Morris LLP

(57) ABSTRACT

Single nucleotide polymorphic sites of the bovine MAP1B, PPP1R11, and DDX4 genes are associated with improved bull fertility as measured by e.g. sire conception rates. Nucleic acid molecules, arrays, kits, methods of genotyping and marker-assisted bovine breeding methods based on these SNPs are disclosed.

9 Claims, 6 Drawing Sheets

Specification includes a Sequence Listing.

```
1081 gagcgcgctc tgcagaggcc gaatagcggt tcgctgggaa accctgggcg gggccgtaag
1141 ggtccagcgg gcgcagactc gggcgcgcgg accgacccgc ccgcagccc cacccgggct
1201 gccgcagtgc cccgcccga tgcacctgcc cccacactg cggcgcccc actgggcgcg
1261 gccggccggg cgtgcgttcc gccggtgctt gggggtgctg tgcgccctct cgtctgcctc
1321 aaccccggctt tgttgcgctc gaagtcccg ggtgggcagc tctgtcctct gcctttccct
1381 ttccccccgg catcgcagac ctcccctct cctgaccga ggtcgcgggt ccctccacaa
1441 cccagcccg cgctctattc tctcggggtg gtgctgaagc gcgtctgcc cgagacacg
1501 gctggtgggc gtggtgcagt ccgcactgcg gtctctacgg cagcccgagg cggacaaagg
1561 gcgttcacgc agccctcgtt ccccacgccc gcccccact cccatgaaa gacgcgagaa
1621 aaccttgttt tagatgaaaa aaaattaaac tctagtggtc tgcctctgca tttgaaaacg
1681 gtcgcctgtg cccagaacaa aaggctgcag ggtggagact cgagttgcag acctggttct
1741 tttgtttaac tttaaagcac tggtgttact ttttggctta aaaaagaaa aaaatgtgag
1801 cagaaagcag acttgttatt ttattcggaa aaaaaaaatg gaagaatagg ctaggtcaat
1861 agtgaaatgc ctcatttgag catctaataa cccttcattt gtcaaactat agtcctttga
1921 atttgatcag tactaatttca gtttatttgc acatttctc cttggaaaat ttcacacgta
1981 ctgactttgg gtgtggctgc tgtatgaatc tatgactttg gattttaaa aaaatattat
2041 ttgtcagcac ttttgctggg aagtaataat aaagcaggtg tgtttctatg tataaaaggt
2101 gcataagcac ccgatgtggt gtgaggagag ggaccctcat ccccatttg gagatggggg
2161 cccagagggg caggaaggat agggagacca gctcaaggtc acaccactca taagtgacag
2221 aatgccggct ctgcagcatc actggttttt ggccgtcat gatgttagtg caggccaggc
2281 gaacatcaca ggaagatcaa agagcaattt ctagagcttg cctttataca aaggcagtag
2341 tcatccactt gtgggcagca cccatgcag ggaggtggct cagcaatcac cttccatgta
2401 attatcttcc tgctttgtta ctctgctgat caccctttta gtgcctatt tctcagggg
2461 tttattgaag ctgcttctgt ttgaggataa actagattca cccaagttat cggtcactgt
2521 gacgtgctct cgactatttt tcacgctact ggaacttagt gatcgagttc aatttgtct
2581 tcttgcccct tttctttttt aaaatttatt gatgtattat gtagtgaggg aaaggctcaa
2641 atcataaacg aggagcttgg tgaattttca caaaagaca tacctgatcc cgatcaagaa
2701 acggacattc ctgggacccc cagaaaccct ctcaggtgtc cttttcagtc agcatgcctt
2761 cctgattttt tagtgccctg atttagtcag cttttttgcgg ggaactctga aatagcagta
2821 ttgatcccat taagaatcaa ccaagtgaat gagcaaagcc atttcctaag gcacagtaac 2881 agatgctgct tttcctctgg agatcaactc tcttgggtcc tggggtcttg gatgcagctc
2941 aaaccacagg gccttccagt gctaaggga aatactgctc ctgtagcttt tctgacagag
3001 atgacttagc aacagggcag gctggctgtt gccctggcct gatatgatgc ttcctcagct
3061 ctcag[a/g]ttcc agcagggcct cctcctccag aggtcactct gataccatgg ctgcggtggc
              SNP1
3121 tggtgcccat gggaccagtt gtgtgaagca agatggagat [g/a]ctccggggg ctcggcctg
                                                SNP2
3181 cttgtgtgcc gcagcctttc cgcagggaaa gcggttcatc ttctgcccct cttgcttgtc
3241 tcccctctca tccggatgag gctctctgag tctggagacc ctagggactt ggattttgc
                                                         SNP3
3301 catttgatga tttaaggctc ta[t/c]gggaaac ctagaaaata aatctgtagg aagatggcgg
3361 aaatgcaagt acatcaatag gcctgaatca gcccaccatg gaggctgagt acatgcttct
3421 tgaaacctac tgttactgaa tcaaactgac tgccatgcagt aaagccaatt
3481 tactgacccc aggttgtggt gaaggaaagt gcagcattat tgtaagatgc tgatgtaagg
3541 agaacgggga gctcgtgctt aagaccccca aaatccccca agggtttcag caaagcattt
3601 ttaaaggcag tgtaagggag ggtgtccag agtgtgtgat cagctcatgc accattctct
3661 aattgagaat tagattgatg atgaggtaac aagactacgt tgggcttcct tgctggctta
3721 gatggtaaag aatctgccta caatgcagga gagctcggtt tgatccctgg gttgagatcc
3781 cttgaagaag ggcatgacaa cacattccag tattcttgcc tggaaaatcc ccatggacag
3841 aggagcctgg tgggtacagt ccatggggtt gcaaagagtt ggacatgact gagtgactag
3901 gcacagcaca agactatgtt aatgaggact atgtgcggat ggtcatcaag tagttaattt
3961 cttccatttg atggtgattt tagcatctga ctggaaaata aggaaaatata cttcagatac
4021 taatatctag gtatttcaga gaggaactaa agcagagggt ataggggagg ggtctgtccc
4081 aggaatgtcc cataaggtcc tgcttggtta cacaaggaca gaagaccatc attcgttct
4141 tcagcttcat tcaaaatgca taatgtaggg tctggtcatt tcttaagtct gaaacaacag
4201 tctttgctca gactggtcta gctttattta gttagttatg caggactcca tgccaaacca
4261 ttgtcactcc ttggcacctc ctttgccccc ttcctaatta gtctccaaca tagacttaac
4321 agtcatcccc gttttagca gagtctcccc tcctccagtt tattttggga tgtagactac
4381 atacactcat gttttgcaaa acgaattcta gagccttgtg aaagttttc attgcttgt
4441 ttatttat ttttaaact aaaacatgta aaaacacta agtgtcagtt tggtttcact
4501 tgctgttaga gtgtaacttt cctctggtta acattgggaa tcagcaggat ttgttcatca
4561 gaaagataga tgtgtgtaac atctactgcc ctgattttt agatgtaagt tttgctaatt
4621 acattgtcat ttattgaata ctttcagtct acattggtta agagaattaa gaacccagga
4681 aagagttagg gctttgtttc catttgtttt taacaggaaa acaacgggt gatgggaatg
4741 aaaagaaatg ttgaggaatg atatatttac tatatccatc catcttcata cgtttcaaaa
4801 tcaaaaggca gatggattc tgcttgcgct gcttaattgg tattatctac tcaaagagtt
```

FIG. 1

```
49681 tccagcctgt tctgtggatg tttgaacttg agaagtgggg tctttgtcca gaggaaacac
49741 tgcttttcgc ctggtagagg atgggctcca tccgaatcat acccagtttg ttccttttgct
49801 acttcttcat cttcccgtgg tttcatgtcg agtcagaatg taaggactgt ttagcttttg
49861 tgaggggcaa aaatgtgttt ttgaactgga caaggtaagg tttgaaccca ttcttttgtc
49921 tttcttgtat acttccattt tcactttgag cacaaagcag gttggggaag caggaggggg
49981 gaagatgtta ttgtggatta gagacagagg aaaaggcagg tgggggttg gaactgaacc
50041 ccactcctg cagcgtttc ccagccggtt ttgaaaagac tctgaaagga gaataacgtc
50101 tttaatcaag agcaatagta ttagctcctt tactataagt aatactttc tttgagccta
50161 tatttatttt accggctag aaatagctga agttattcca gcagccatga ctattgtcta
50221 ggagttggat gtgggctggc aatagactgg ctgattacac tgtttagaaa taaaccccct
50281 tgttggcagt ctcttctggt gagaatggtt cataaaggtc cctgtggctg gttgttccat
50341 ggtgcttgct tttatatcag ttcagtaccc tcataatgag gtggtcttct agaatatatt
50401 attataactc tgttgcagag ggcgtagggc tcgtcagtta tgcaggcaac atcacaaagc
50461 tttggaagaa atctcttaat taagtgctag ggctggtgct gcagtgaagg gatgaatgga
50521 ctgaaatgct tcaatctctg agcgtcttt caaactaaac gggccctttg ccgcatcata
50581 gccaggagtc cagcagacgg acacactgga aaagtggtgg tggatgtgat tggtgatgtt
50641 cctgacttcc tctgacctac ccctgggat ttctgtactt cacgtcacac gtggctcctt
50701 gttgatggta tggtgaaaac ataggtgttg aaagaaccag aattgacagc agttcagcga
50761 ccttttgggt cttcaggtct gagaccatac cctaggcagc atcagtccct ccacggtaga
50821 tggcactgga ctttctgtgg cgtttaagac ctaacgttct gtgactgaga atgtggcctg
50881 tcttggccac agctggtacg atgacaagat gactatctga gttaggaaga aaaagtgaag
50941 tgaaagtcat ttagttgtgt ccgactccgt gacctgcagc tcttctaggc tcctctaggc
51001 tcctctgtcc acgggatttt ccaggcaaga ataatggagt gggttgccat ttcctcctcc
51061 agatcttccc aacccaggtc tcctgctttg caggcagatt cgttatgtgt ctacaatgaa
51121 agaaagggta ggagcaaata cagaggcaga agtttgttcc ctcctaggaa ggttatcctt
51181 gatctggcca ttcaaagacc ttttcatttc ctctcagatc ttttcaaagt gactaacctg
51241 aaaaaatctt gatgtgtgga ccaggacatg atggaggaag gcatctttt cttcctttt
51301 actccttgga gaagagatga aactaaaagg gctcaaggg aaaaaaaaaa attcttaaaa
51361 aaaaaaagtt aataaaaaaa caaaagtaa taaatagctc tttgtaaaca gcttaccacc
51421 ttacttcctg tggttacatg cattacctta tggtcgtgat tatgaaagat ttctagagaa
51481 acgttaggat gatcacataa ctccctccta aggcgccagt ggagccaaa gtctttgctg
51541 ttcacgtgcc ttgtgagtgg cccaacacag tggggacttt ataaatatca aatcattgtc
51601 gttaaaaaac acttcccgct tcactctgag acccttcctt ttaaggagtg catgtggtgg
51661 [g/a]ggaggatta atgacagcac agcgagtgtg gcttgaaggt ggtgacatca ccggcttga
       SNP3
51721 acccttcagt gccgggtgag aggattttca tctcatccat cctcctgagt ttgcca[c/t]gag
                                                                     SNP4
51781 gggtctccaa gaacaggaaa agaggagtct gaggagagga gacttctgga cattctgtga
51841 tagtccctg gctctgtgcc gtattgtttt gtaaataagg cagttatggt ttctagtctg
51901 ttgtttttct acaaaaatgg aggacgtgtg accagcagtg ttagccttcg tgaatgagat
51961 tctgtgtttc ggccatcact ggttcaagta ggtaacctaa gagctgagct taagttgctt
52021 ctcttgcagc ccatctttgg ctttcagtaa ggaatctgag caacattaga ctgagaatca
52081 gacacctta ccatcacttt acgggatgct tccatttgct gtgtgatagg acgcaggtgc
52141 aggagggagg cgtctggacc ccagagtcgt ggcgtcagga ggtccgtgg gagcatcctc
52201 agcctctgca gtggtcctac caggagagga aggtgcttgg gtgtcgggat acccatgctc
52261 aactcctggt tctcccgtta tcatgccctg tgactctgga caagtcactt agcctctctg
52321 aaccttaatg tttgtatctg ttaagacaag ggtttggaat agatccgtcc aaattcacat
52381 ttctgcagac ctgggttact ggctgtaggg ctctaattgg actggatctc ctcatccctg
52441 ataacctatt tccagggcgt ggggccccct gctgtacagc gtcttgcttc attttcccac
52501 cgtcttttag ctcccatctg gatgccatct tctgtgtagt atggaagcct tcctaaacca
52561 tccagtgact ccttgagcc cttcctctcc ctgctgaggt gtgtgtccag gagccagggg
52621 ccatcctgcc ctttttgctg gccactgccc catgttctg gtctcatgcc agggtcggca
52681 ctctgtcagg atgtggtggg ttgagtttat acctgatctt gatgtaaaca catggcctct
52741 gccagtcat ttgttcctgt tcccacactg gcttccagct cttttgtgga ctctgactct
52801 ctgctctcct ggcctcctga tggctggaca tcttttcttt tccttctaga atgccacccc
52861 ttttttgtt gtctaacttg taaaagcccc atagatcatc tcccatttca aaccttaga
52921 gatgactatc ttgatatgtt gataagaggt gaacttctc agaggagttt cttgttacag
52981 tgtcaaatgt ggttataaat cactggaact taaggatctg tctgccaagc agtagacacg
53041 agtttgatcc ctgggtcagg aagatccgct gaagaaggga atggctatcc atgccagtat
53101 tcttgcctgg agaatcccat ggacagagga acctggaggc tacagtctat ggtgtcacca
53161 aaaattgga catgacttag tgactaaaca acaacaataa gagaagcttt aagggaggtc
53221 agccctctct ccaccccagc actagaacag tccctagagc agagtctccc aaatctgcct
53281 ggtgagcaga atcatcaccc agtgcttta ttattatttt aatatttatt aaaaaatttt
53341 ttttgtttgg ctatattagg tcttagttgt ggcatgaggg atctttagtt gcaacatgtg
```

FIG. 2

```
85081 agtgtctgg ttaatcaacc agtgaggtca gctgaccact gggtacccag tacagattga
85141 gaaaagagca tccaagactc tacttattcc attctgacca cactgcctca ctaatacaga
85201 ctcaacatct tgttttaggt cgaaattcag cttggcaaga gcaagcatcc ctgacttcat
85261 gttcttagac ttatcaagtt ctcggcagtg atctgggttt ttgatgaatc tgggtttctg
85321 atgatccagc ttcattttgt tgcttcaaaa caatcacagg gatttgaatt catatatttt
85381 atttgcttta catagttact tgaaggtttt agatcacagt tcacaaacat gtaaagcaaa
85441 aaataagcaa cactttcttg atttattatg gaaaaattca gtatttagta ctttaggaag
85501 tactagttac aggtacaagt ttttactttt aggcaacgtg aagcagcaat ttcaagactc
85561 atatcagatt tcctcttttt atttgcacat agaaaacaaa ctgaatttgt tcatgcttag
85621 aatttgtata gagccaccag ataataaatc ttgatctaaa ggacttaaca gtgaccatgc
85681 acttaggaga aaacatgaaa tcaattcaaa cagataaaaa cccaactgaa atttgctgcc
85741 aaactcatga aacttacact atagcccaca caattgattt tatcacttttt ttttttttg
85801 gtcatttaaa gataattttg agggaaagtg agttaatttg aatttacatt gaggatgctt
85861 tcccaacaga ttttttttaaa agacaaaact gcactattaa ttaattttaa aacaaacctg
85921 ggtcaacttc cagtggttct atcagttcgg gcttctatga gcaatgttca tttggtgtca
85981 acgggagtga ttcaaggtgc aagtggaaac tgcaggcatt taaaaatatt agatgatctg
86041 taactcacaa acctctgcta caagtcagaa ttctttggga gattcacaca tgaatatgtt
86101 taggactttt agcttaggtt cattataatg gctggttaat ctattcatga aatgattcag
86161 tttatccaaa taccagtttg gctgattctt actacccct gccctccaaa ataaaaataa
86221 accagttcat agctgatttt gactgtggga tggcagtctc tatacatccc atggagaaag
86281 gcaagagaat taaatttagg ggatctttgct agtatttttaa gtggtttcac agcagtggtc
86341 tcaaaccaga tacacattag cattggctgg gatgctttta aaaagtgatg gtaccctggt
86401 cagtgaagcc ttaccatagc cattgaagcc agggcatctg tattaagcat gctaagtgat
86461 tctaatcatg tggccaggag gaagaaccac tgccttacaa tgctagttct gttaatgttt
86521 caaccttctg attagaacaa atcagaaagc caattctaga aacaaggtag ccagaaactg
86581 agattaatct gaaccttcat tttgcccagg ctttctgact tgggggaat ttt ggctgtg
86641 acataccta cccttacctc agtccggtat gttctgattg gctagagaaa gcagagtctt SNPs
86701 tctgaaccttt cctgttgcta aagtttggta tctagtcttg tctaaggaga gacgtctacc
86761 atttagagga ctgtcctaag gagagaatac agtgttttca tcagtttatg catgaggctg
86821 aggtgctgag ggtcttggag atcatatgac attaagatct gactactggc tagatcaaat
86881 gtgaggggat aatattcagc tgtgggccaa actgctttta aatgaaatcc taacatgaat
86941 tactaagatg gcttaactat gcttaccaa atgcagatgc ttcctttgt cctttaaaat
87001 ctattcttta gatcacattt caaattaaaa gacacactag cagccttt aggagtgtta
87061 gcgtctagtt [c/t] tatctttgg ggaaagcctt ggcaactctt cttaattgct aatgtgttta SNPs
87121 agggaaacgc cccattcttc atttctcctg agatggtaaa cagtcaagtg atgctgtctc
87181 agactgccag tgtcaaatgc cctctgtgag agagggggagt gccaacacc actcccatgt
87241 cccagagcgc cttctgggga ataagtaggg aagtctg ct ggacagatga gtctctttgc
87301 attttttgtga ccctggcctt ctctttgttt ttatttgttt acaaagggcc aggaaccacc
87361 aagacgtcca agccctcagc tgtgccccca ggccccctg tgtacctgga cctatgctat
87421 attccaacc atagcaatag taagaatgtc gacgttgaat ttttcaagag agtgagatcg
87481 tcctactacg tggtgagtgg gaacgaccct gctgctgagg agcccagccg ggctgtcttg
87541 gatgccttgc tggaagggaa agcccagtgg ggcagcaaca tgcaggtaag agttccagga
87601 cggtgtttgc acaacacgtg gagctgtgtc cagaggcagc aggaagggat cgtgtttaat
87661 gaggcaccac cgtggatccc catgaggtgc ccacagggcc tgctgcactt ggacaaagtg
87721 gatttcacac acacaagtcg gtctaaaagc attcgcgcca ccagccacca tggacttgga
87781 ggaaggccac tttaccaccc taaagtataa tctgcagagt gggcccaaga ttacacaccg
87841 ttcatatacc aagaaaatta accagcgtaa ccaagtgtca tatttccatg tgagatggat
87901 aaagattagc ctttacttgt ctttcccaag tagacaaaag ctagagatat ggccatttag
87961 aaaatcagct gtccacatga gattctgcag gagcactgct gaaaatggtc ctcagcagga
88021 cactcccaac acccaaacat cgtaatgagc cacaaccac tcattattc agttatggat
88081 tttatctaag ttttacttac ggttttgtat agtgatctag taaactgtat ttgcataacg
88141 ttaaatagaa atcctggtta tttcattata tgaaatctaa tgcactcagt ggcctcttac
88201 tgaatactag gtagaattta agctagtaat cacttaccca ccccactcct ctgtccccaa
88261 acacacacac aaagacataa atcttgctc tcatgataaa atgttagtta acatgcaatt
88321 agaaggtttt cggctgcatt aataactaaa gccctttgt tttaaatatg caatatcttt
88381 aatgtaaaac atcagttgtg ttaagaaaaa tacaagaaat tccaccttaa ctgaagaact
88441 tctcataatg ctaaagaatt gaaactgat atagatgaac taactggcta gtcatgactt
88501 gcttttggtt ctagtcttca actgcccag aaaaactaat ttttagcag ctttattctg
88561 gttcctagaa aatgtaagtt ggaaagtcct atggattttc taaggacaat agaatatttt
88621 tctctttccc tttcttttc taatggtcta attaatacct tactgctgtt ctatttttcc
88681 ccaccccatt tctggttctg ctcttcagta gctgttttct ctctccctgc aggtgaccct
88741 gatccgact catgactcag aagtgatgag ggaatggtac caggagaccc atgagaaaca
88801 gcaggacctc aacatcatgg ttttacagcc cagcagcaca gtgttatgc aagatgaatc
88861 cttccctgca tgcaagatcg aactgtaaca accaaggtca gccgcaccac aggatttgaa
88921 ctttgtttcc agaaattctt cgatttgaaa ccaccttttc taaaaaaaaa gtcaattcat
```

FIG. 3

```
-120 gcggcgcctg cgcactgtca cattacggcg gaactaatcc ggcgacccag cgctttgacg
 -60 catttagtac caggaaggga aaggggggac cacagaacgc gtcacacccg gaagtaggga
   1 gccggaactg gggttggaca ggttatccc  aggggtgggg cagcggaggc ccaggaggag
  61 ggggaaaaaa gaaggtggag gatcctggct gctaatctga atcgataccg a[t/g]tctcttag
                                                              SNP1
 121 acctcagaga cacagaaaag acagaaggt gcctcatccc ctttcctccg cttctctctc
 181 tcctcagcct tagccatggc ggaggcaggg gccgggctga gtgagaccgt cactgagaca
 241 acggttaccg tgacaacgga gcccgtgaga aaggctgggg gcggtgctgt ttaggggtct
 301 gagagatacc gggagggaag ggataaggct ttggagagtt gctggatggg ctgggcctgg
 361 ggatatggga ggaagtgggt ttgggagaat cgcagagtat taggggattt ttggtgtgtc
 421 agagttggtg cagaaggctg gtcaagtgac atgcaataga gttaagatgt aggtgatact
 481 gcttgggatg gtggtgtctg taagtattga aagactggga acttggcgat taatgagcaa
 541 gggatgtact gggggaaatg aagggttgtg tgagaaagca tggttggaag ctcgctgtag
 601 ggaaacttga cactaagcat gcttatcaat aaatatttct tgaagagatt attgcaaacg
 661 gaagcagagg gaatgaggga acaagaaaag ggagatgatg ggagtatttt gaaaaatcag
 721 agatgtagag aaaaacagcg ttttttgcaaa aacattgctt tcaataggag atgttcctgt
 781 cgggcttaat aacccttttga ttaagggagt ttagagtaat agttactaga gatgccagga
 841 tgctggagaa taggtggata acagattggg agggctgggc ttgaggatga gagatgtgag
 901 aacagagtca tttctttaat gggaaaaaga ataggcgttc tgggaaaaga aagggagatc
 961 aaagtttagg cattggtgac tgaaaaaata atttttcatgt attaatacca ccaaagatga
1021 tttggggagg aagatggagg aacagcgagg attatatttt cctttgaaga tttgctggga
1081 cttttccctag gttaggaatt gtatcttctc tgtatactag tggttactaa gaatactaag
1141 aacagaattc ctcaagggac tccttgaggt caaaaactg ttctatatcc tcccagcatc
1201 agctcctctg t[a/t]gctgtgtt tgtgatcctg attgaactgg gaaagggaag aaaggaggcc
                SNP4
1261 ccagggagga cgcaggaaga gttagtagga ggggactagc taggtatgcc tatcttctt
1321 aaccttccag gagaaccgga gcctaaccat caaacttcgg aaacggaagc cagagaaaaa
1381 ggtggaatgg acgagtgaca ctgtggacaa tgaacacatg ggccgccgct catcaaaatg
1441 tgagtaattg ttgccccaca gtaacgctga agtcctggct cccct[a/c]agca tatcttttgc
                                                      SNP2
1501 cttcaggcat tcactggcct tccaaagcc ccagatg[c/t]t cacagtcctg tggctgcctt
                                                  SNP3
1561 ggtggttctc tgttatcagg gagaggaggt taaagttaga gggaaagagg taggggaggg
1621 cttcaatttc catgtgcaag gcctaaagtc aaaggtatct gaggtgggag aagaggagct
1681 ttggattccc ggctggaaag gcaaggtggg taggtgacag agtcccagag tgtaggcctg
1741 gggaagctgg atctggaagg tagaaggaga aaatggtggg aagtaggaat tttgactgag
1801 atccagtggg aatggaactg acactacatc tgaactcttc ctcctttttc actgggctcc
1861 tccatccaaa tccaggctgc tgtatttatg agaaacctcg ggcctttggc gagagctcca
1921 cagagagtga tgacgaggaa gaggagggct gtggtcacac acactgtgtg cggggccacc
1981 gcaaaggacg gcgtcatgca accccgggac caagcccac cagccctccc cagcctcctg
2041 accccctcccca gccccctcca gggccaatgc agcactaaat tcctcgctcc cccaccattc
2101 ctgtgtctgt ctggccctga atgtattcat gtggctactc ggggactaaa cccacgattt
2161 gatccttct ccagccccct cctcccctct cctctgcctg acagagggaa gagggagagg
2221 aaggtggaca gagatcctgg aattctgact tgctgctatt ccagaaccta ggcttctggg
2281 ttccccagc cctcatttct ccttacaata cccagcctcc tctctccagg gatccaggca
2341 tcttgatccc aatcttttc ctttgttctc actgccaaac tgcctgtcct gggatccagt
2401 tatcttggcc cctttcactc tctacttgag ttccaaacag ctaaattggg tttccagcag
2461 cccagcttt cactgccagg gtcctagtca gattccaggc aatcttgctc cagctatgct
2521 tgttaatcct ggcttagagc tcttccactt atgtatttat gtcatcctaa ctcttagtcg
2581 ttgcctgtgg gatgtgaggt cttctgtgag acctcagggc tcctagccct ttcccttctc
2641 tcctgcccac ttcccccaag cccttaagag gagttaggag agagggaggt ctttgtcctt
2701 ctcacctta atgagaaatg gaaaaagaa atgggcatgt ctctctcct caccgttctc
2761 atgtgactag ggtttctgac aaaactggct ccaagactag tcacttagag cccactatct
2821 cctcagcctt tggtcttcca acttaggaga cagatccgac ccaggggcct gggtccctgg
2881 gagaggatgg aaaagggagg gagccaagag atgcaatctc acccctcct tccaaggcct
```

FIG. 4

```
32101 gagtgaggcc ctggatcctg tatttaaaag cctccctgct gactctgatg cctctttcat
32161 ttggtaacca ctgatctatg gagtctttat aacttctctg cacacagatg tatagtgtat
32221 tttgtggtta tttttcccgt atcttgtgtc ccttagctgg tccagtatag taataaggag
32281 ctcagatttt ggaatcagac accgggatt tgagacccag atccttctct tcctgtcagt
32341 tgtattattt taaaaaagca tgtttaactt tgtatttctt ttttctgtt tataaattga
32401 ggataatacc cacctcataa ggttttttgtg aggatttaaa aagttaaaat agaattcatt
32461 tagaagagtg tcagatggat actgtttat gtgttattat tacattattt ttctataatt
32521 agtagattat aactgatctt gggatcatta tctcattttt gtttgtgctt aactttattt
32581 ttaactctac agagattatt ttttaataac tttttatttt gaaatcattt gactcaagaa
32641 gtttcaaaaa tagtacagaa gatttccttc agcttgcctc taatgtaatt gtactcctca
32701 cccagtttct cctaatgtca ttagcctatt ttaattccca gtgtggtcaa aataactgta
32761 agtttgtttg aggagaacag ttggccaaag gttatgtgag gtgggttttc tttcatatat
32821 gacaataaat gttagctacc atcatcatta ttccagatga tgatgaatta ttatatcatc
32881 aaataataat tccattattc cagattattc taagaatctt tgcagaattc tttctttcct
32941 cttcaaccc cttgtatgaa atctttgctt ctgagaaggt tgtcttgatg ttaaatgatt
33001 ctttaggaat attgtcaatt gttgatgtca gctcaaatag gagcctgcaa caagagctgt
33061 gggtcattgt ttattataaa tcaatattaa ttgagtagat tagtactttt gtacataaac
33121 aactgatagc ttttaatctg tcgagccaca tatgtcatca ctgggaccta gttctctggc
33181 actaaatgtt agtgatatgt acaagattc cttgaaacca tcttggtatt ttccaaatat
33241 gggtttattg gaatcttcta gaaagcttaa agttattact gaaagttata tcaataaggt
33301 ataattttt aatttagaaa aattgttcat tcctggatat cactctgcac attcaaaatg
33361 aatctctcta gggtgggttc tgataattta ttttaacca actttctga taattttag
33421 tcatccttca gtgtagtgat cctcatacta ctatgtataa actctggtaa tgttacttaa
33481 taatgtcact aaggacagaa agccgggatg tccccaaatg cttccattag gatggatagg
33541 gaaaagtttg catatattaa aaaacacta taatgcctca ggttattaa gaaagacaat
33601 ttacagatta atgatgacat tataaataca atagttatgc atttctgaga tccgtttgac
33661 tactcaactg ttcagatatt tctgaaactg tttcgtgaca tttatgaaat tcttattttt
33721 tggctgtgct cagaacttga cagataacat gcttaacatt tagtatttag gtatattagg
33781 tgatttttaa aaagaattga ctgaataatg tgtttgtatt ttgttgttat ggtgatttta
33841 aaatttaaaa ttttgttcat atgttagctt atgaatatat tttttctcag taatttctct
33901 tgtgatagta ctatttagat actacagtaa tataaatact gcaataatta tttagatgct
33961 attcacatgt taaattttta ttcaagaatc tagtattgac tgtgaagata atcaacacg
34021 gaacagaggg ttttccaaga gaggcggtaa ggaccatgtt ttggaacaac ttgtacttaa
34081 gacagaaatt aaactgaaaa attgattttg gaagagctga aagaaaaatt ctggtggtga
34141 aaaccttca agaaaaatac tttggcatat cctttatgct gttaatattt gagttaatat
34201 tcagtaggtg tctctccttc tgctttctga tgtcactc[g/a]a tttgtctttt cctaagacct
                                          SNP2
34261 ccagagtgtt ctatgaacta caaaaggtgg gactgtgtga atcttggtca ttcacagtat
34321 agataaactg ggatgtcttt gtctctgagt aggaacattg gagatatggg ggaagggaga
34381 agttgtagat taattacat acttgctaat cctgcctctg cttgaggtga gatggtataa
34441 aaattatagt gctcagttct ggattatcta taggcagaca tgttaaaata gcaacaatat
34501 ccacgaaaaa ccacagtgaa cttataaaat tgctacaagt gtgcaaatat atttatgata
34561 gaacttagt gtttggagct gcactagata catcatagtt tttgctgcaa cttggagata
34621 tcgttttccc ttgcctatta gatgattggc tcattgaata gatcattgaa tagcaggcct
34681 tcctagtgaa gctgagactt gctgtggatt tcactatagc cttggatgag ttgtgagggg
34741 cggtgggtag gaatttggtg gtgaatcagt tcagtcgctc agttgtgtct gactctttgc
34801 gacccatga attgcagcat gccaggcctc cctgtccatc accgactcct ggagttcatt
34861 caaactcaag tccatccagt cggtgacgtga atccaaccat ctcatcctct gttgtcccct
34921 tctcctcctg ccccccaatcc ctccagcat cacagtcttt tccaatgagt cagctcttcg
34981 catgaggtgg ccaaagtact ggagtttcag cttagcatc attccttcca aagaacaccc
35041 aggactgatc tccttagaa tggactagtt ggatctcctt gcagtccaag ggactctcaa
35101 gagtctttc caacaccaca gttcaaaagc atcaattctt cggcgctcag ctttcttcac
35161 agtccaactc tcacatccat atatgaccac tggaaaaacc atagccttga ctatatggac
35221 ctttgttggc aaagtaatgt ctctgctttt cagtatgcta tctaggttgg tcataacttt
35281 ccttccaagg agtaagcgtc ttttaattc acagctgcag tcaccatctg cagtgatttt
35341 ggagcccaga aaataaagt ctgccactgt ttccactgtt tcccatcta tttcccatga
35401 agtgatggga ccagatgcca tgatctttgt tttctgaatg ttgagcttta agccaacttt
35461 ttcactctcc tcttcactt tcatcaagag gcttttagt tcctcttcac ttctgcata
35521 agctgagtct ttaatggcaa ttgtaggggg ccctgcaatg atgggcgga catttagtta
35581 agaaatagac tcgtctttta acattgctct ccttcccct taacaagga gttttgacac
35641 taatgttcct aaaacatagc tctttggtt ttctgcagaa cagtggctat ctttcttact
35701 attcagtttt ctttaaatca ttttaattca tatttaagtg cagcaatgaa aagccagttg
35761 cagctctttg tgcttgatcc tgacttattg actagtgtag gttgtctagt agggtgtccc
35821 tgattgctat tttctttaga tgtatacatt tgaaggtaga aaacttgtgt gtgacacggt
35881 ggtcactcag taaatacaga tgtgtgtgta aatagaacct tatctaaagtt tatgttgaag
35941 tatcatgtca tacaggaaca ggttggtgca tatgtcataa atgtatacag ctcagtgatt
```

FIG. 5

```
59641 ctgatatctg agattaaata tcacctctaa aaccttcctt ttttgcagtc ctactatctt
59701 acttaggaaa ttccattcag tatcttgccg ggagaattcc agggacagag gtgcctggtg
59761 ggctatagtc catggggtca caaagaatca atggacatg actgagcgac tgacactcat
59821 tccagttgtt cagacacaaa aatatgaggc atcttgatt tcttctcca gtgtacatat
59881 ctgatctgtc agcagagtc tcttgttct gtctagcatc aaactatatc agaacccatc
59941 agttgctaag ttaaaacaaa gatcagatct acttcttgcc tccaaccca atggcttcc
60001 tcctcaaagt aaagatcttt cagtggattt caaggcactt catgaaatgg cttccatcat
60061 ccctctccaa atcctgctgc tctccattgc ttaccctatt ctagctgcac tttgctcatt
60121 actcatccc acacgtacca gacatggttc tacctcattg cctttgttct tgatattcc
60181 tctgcctaga acgtaaaaac cagatgggga cctcttttct ggtttgtttg tttgtttgtg
60241 agcacgtaaa gaacacctat acctttagaac ctttatattt gttcttacct ctgacctata
60301 atattgtttc ttcagatatc tgaatagttc acttgtttag taatatctgt cctcagatgt
60361 catctaatta gagaaggtgc ataaacccat ttggccctt atcctgctaa atttttttct
60421 tttttagact taatgcatca tatttgttat ttacctctcc acaatgagtg cagatgcttt
60481 gttttatttg ctgtgttttc agtatctaga atagatactg gcatctactg ggtgctaaat
60541 gtttgttaat aaatggagac agctgatagg gacatggagg agtgggatta caaaaagtaa
60601 caccctgtta cttctattca ggctatagat tattatcttt cctctctaac attttataga
60661 aaatttcttg gtgtggaaga gtcttttgct catgcttata tttaaaccaa ttaacaaagc
60721 taacaagtaa atattcttta atgtgttaag accctgagat aatatcttat atatctatat
60781 ataaagata ctttgggat taaggggttt gaattgagat aatgttgaaa cataaatat
60841 tgtagagttt gtcagccctg ggtgaatgc tattattatg aatgcctctg gcagtcaagg
60901 taaaataata gattctataa ccatgggaag aacaaaggaa tttatttata gagagggaaa
60961 tgaagggctg gagccaaatt tggaactgct aagagttggc aggtagatat catttatctt
61021 tccctaagtc tctacttatt ggttggccta tgaaggcaag gggcaagcgg tcgttttttct
61081 tttttttag tcataaagta ggaaaaagtc cttgtctctc tatcttgac attttatccac
61141 tcaggaaata tttgaattgc tcttaacctat caggcctgag tttaggtgct gggaatacag
61201 tggtgaataa gacagtttcc tactcacccct atgctttttt ttctttttcct aattttgtag
61261 tttgaatgtt tcattgtctt gtaggtgatg aaagaactat ggtctttgtt gaaactaaga
61321 aaaagcaga ttttattgcc acttttcttt gtcaagaaaa aatatcaaca acaagtattc
61381 atgggtgagt agattattat gatttcctag taaggaggta acttctattt gtcatttgtt
61441 aagaaatgtt ggtatattta actagtaaaa aatcctggaa ttaggatctc aagatctagc
61501 tattattctt catctttaag ttttttataag aacaagtcag ctgggatgga tgagttagaa
61561 gtatcttaag ttcctcatca tgattatcaa gcagtctcac ttagtctctc taatccttag
61621 atctaggtgc ttattcagct aatcttattcca gtgcttggta tttttttcac tgggcctcaa
61681 aaatgtcata gtaacacaac ttcattggca ctttactagg agatctaaaa tattaattgg
61741 tgaatatgta gaattccgag attatacttt taaaaaatca ggaattttg agaaaggatt
61801 tgatcaacta gttgtgtatt ttttgtcaaa actagaaaca gtttattagt tggtaagatt
61861 tgatgtctgt cgcattgag tctgtatttt ggctgtaggt attagctgtc accttccatct
61921 gcaaatggag ttaattgtcc taacctcaaa gtattattgt gagaattaaa tgatgacttta
61981 caagaaatta gtataatact ttgtatgtaa gaagtagaca ttaatgttaa ctgttgctat
62041 tttttgtttta ctgttatcca ttgaacttat ccaaaaagaa atctatccat tgaactttaa
62101 tggttgtctt taatagttt cttaagggct attctaatac atgcttttgtt ttcttttcaag
62161 tgatcgtgaa cagagagaaa gagagcaagc tcttggagat ttccgctgtg gaaagtgccc
62221 tgttcttgtt gctacttcag tagctgcccg agggctggat attgaaaatg ttcagcatgt
62281 tattaattttt gatcttcctt ctaccattga tgaatatgtt catcgaattg ggcgtactgg
62341 tcgttgtgga aatactgca gagctattc ctttttgat ctggaatcag atagccagtt
62401 agcacagcct ctagtgaaag tgctatcaga tgtaagtttt taattttta aactgaatgg
62461 atagtgttct tacctttgtca ttgaaagcag acatttttata tgtatggatt ttcagttcag
62521 ttcatttgct cagtcgtgtc tgactctttg caacccatg gactgcagta tgccaggctt
62581 ccctgtccat caccaactcc cagagcttac tgaactcat gtccatcgag ttggtgatgc
62641 catccaaccg tctcatcttc tgtcatcccc ttctcctcct gccttcaatc tttgccagca
62701 tcagggtctt ttccaatgag tcagttcttt gcatcaggtg gccagagtat tggagcttca
62761 gcttcagcat cagtccttgc gatgaatatt caggactgat ttccttttagg gttgactggt
62821 ttgatctcct tgtagtccga gagactcaag agtcttctcc aacatcacag ttcaaaagca
62881 tcaattcttc agcactcagt tttctttgaa gtccacttct cacatccata catgactact
62941 gaagaaacca tagctttgac cagacagacc tttgtggca aaataatgtc tctggttttt
63001 aatatgctgt ctaggttggt catagctttt ctgcttttct tccaggagc aagcatcttt
63061 taatttcatg gctgtagtca ccatctgtag tgatttcgga gcccccaaaa ataaagtctc
63121 tcactgttttc cattgtttct ccatctgttt gccctgaatt gatgcgaccg gatgccatga
63181 tcttagttttt ctgaatgttg agcttcaagc caacttttttc actctctttct ttcacttcca
63241 tcaagaggct cttagttct tgcttctg ccataagggt ggtgtcgtct gcgtatctca
63301 ggttattgat atttctccag gcagtcttga ttctaccttg tgcttcatcc agcccagcat
63361 ttcacatgat gtactctaaa atccacgggg cggaggagcc tggtaggctg cagtccatgg
63421 ggtcgctaag agtcggacac gactgagtga cttcacttttc acttttcact ttcatgcatt
63481 tgaggaggaa atggcaaacc actccagtgt tcttgcctgg agaatcccag ggacggggga
63541 gcctggtggg ctgccgtcta tgggttgca cagagtcgga caagactcaa gcgacttagc
63601 agcagcagca tataaattaa ataagcaggg tgacaatata cggccttgac atactccttt
63661 cccctatttgg aaccagtctg ttgttccatg tccagttcta actgttgctt cttgatctgc
```

SINGLE NUCLEOTIDE POLYMORPHISMS ASSOCIATED WITH BULL FERTILITY

CROSS-REFERENCE TO RELATED APPLICATION

This is a divisional application of U.S. application Ser. No. 14/754,729 filed on Jun. 30, 2015, claiming priority to U.S. patent application Ser. No. 13/798,181, filed on Mar. 13, 2013, the entire disclosure of which is incorporated herein by reference.

STATEMENT OF GOVERNMENT INTEREST

This invention was made with government support under 12-CRHF-0-6055 awarded by the USDA/NIFA. The government has certain rights in the invention.

FIELD OF THE INVENTION

The present invention relates to compositions and methods for testing and selecting cattle using molecular genetic methods by assaying for the presence of at least one genetic marker indicative of increased bull fertility. Specifically, genetic variations in the MAP1B and PPP1R11 genes are tested and used for selecting cattle animals with improved blastocyst or fertilization rates, or both.

BACKGROUND OF THE INVENTION

The dairy cattle genome has been significantly restructured over the past 30 years due to intensive breeding effort selecting for production traits, including high quality milk and high and sustained productivity. However, while those efforts led to dramatic improvement of productivity, there has been significant reproductive deterioration in high-producing dairy cows, which in turn has caused substantial economic loss in the dairy cattle industry (Lucy, 2007, Fertility in high-producing dairy cows: reasons for decline and corrective strategies for sustainable improvement. *Society of Reproduction and Fertility Supplement*. 64 237-254). Key factors contributing to decreasing fertility of dairy cow are low fertilization rates and decreased embryonic survival.

Fertility is a complex trait that comprises developmental stages such as combining sperm and egg to form a zygote, compaction of embryo cells to form a morula, establishment of the blastocyst, attachment of the embryo to the uterus, and fetal development (Amann and DeJarnette, 2012). This complexity makes accurate prediction of successful pregnancy difficult, as aberrant development of sperm, oocyte, embryo, or fetus all would lead to conception failure. Conception rate in dairy cattle is about 40%, and only 50% of the fertilized eggs produce viable embryos (Santos et al., 2004). The decline in reproductive performance in cattle over the past few decades (Dobson et al., 2007) has been ascribed primarily to fertilization failure and early embryonic loss (Santos et al., 2004).

Previous studies have shown that genetic makeup of an individual plays crucial roles in embryonic development and reproductive success (Weigel, 2006; Shook, 2006). Although a male and female parent each contributes half of its genetic material to the new zygote and both are necessary for embryo development, it is not obvious whether or not this contribution is equally important to pregnancy success. For example, it is well established that the paternal genome supports growth of extra-embryonic tissues while the maternal genome fosters development of the embryo proper (Barton et al., 1984). After fertilization, the development of an embryo is controlled by maternal genomic information that is accumulated during oogenesis (Telford et al., 1990). It is only at the 8-cell stage in the bovine embryo that the embryonic genome activates and the embryo switches to transcribing its own RNA (Memili and First, 2000).

Despite that most breeding schemes in cattle are focused on the selection of elite bulls using progeny testing or genomic selection, and that some semen traits (e.g., sperm motility and percentage of abnormal sperm) show moderate to high heritabilities (Druet et al., 2009), most fertility studies in cattle have focused on the maternal contribution, and the paternal contribution to reproductive performance has not been thoroughly investigated, and only a few studies have been reported in the literature (Feugang et al., 2009; Khatib et al., 2010; Peñagaricano et al., 2012). Therefore, characterization of bull fertility markers is both feasible and highly desirable, and the deployment of these markers in cattle breeding would lead to improved reproductive performance in cattle.

A recent comparative genomics study has characterized many genes involved in the control of spermatogenesis that were highly conserved from fly to human (Bonilla and Xu, 2008). Some of these genes were reported to be crucial for human fertility. However, it is not known whether or not these spermatogenesis genes play important roles in the fertility of bulls.

SUMMARY OF THE INVENTION

The present inventor carried out an association analysis between highly conserved spermatogenesis genes and sire conception rate (SCR) as a measure of bull fertility, with the objective that significant polymorphisms associated with bull fertility can be used as genetic markers in breeding programs aimed at improving reproductive performance in cattle.

Specifically, an association analysis is performed between highly conserved spermatogenesis genes and SCR in US Holstein populations as a measure of bull fertility. Sequence analysis revealed 24 single nucleotide polymorphisms (SNPs) in 9 genes in the bull population using the pooled DNA sequencing approach. These 9 genes were selected for their high level of sequence conservation between flies and humans. Overall, the 24 SNPs were tested for association with SCR in a population of 1,988 bulls. Three SNPs located in the MAP1B gene, one SNP in the PPP1R11 gene and one SNP in the DDX4 gene showed significant associations with SCR. Nucleotide probes based upon these SNPs are found to be useful for genetic testing of bull animals for improved fertilization rate.

Accordingly, in one embodiment, the present invention provides an isolated oligo- or poly-nucleotide molecule consisting of 1) a nucleotide of Position 3066 of SEQ ID NO:1 and at least 12, but not more than 200 contiguous nucleotides of FIG. 1 adjacent to position 3066;
2) Position 3323 of SEQ ID NO:1 and at least 12, but not more than 200 contiguous nucleotides of FIG. 1 adjacent to position 3323;
3) Position 87071 of SEQ ID NO:2 and at least 12, but not more than 200 contiguous nucleotides of FIG. 3 adjacent to position 87071,
(4) Position 112 of SEQ ID NO:3 and at least 12, but not more than 200 contiguous nucleotides of SEQ ID NO:3 adjacent to position 112, (5) Position 61646 of SEQ ID NO:4 and at least 12, but not more than 200 contiguous nucleotides of FIG. 6 adjacent to position 61646, and 6) Position 34239 of SEQ ID NO:5 and at least 12, but not more than 200 contiguous nucleotides of FIG. 5 adjacent to position 61646.

In one embodiment, the nucleotide molecule of the present invention comprises at least about 15 contiguous nucleotides adjacent to its respective position (hereinafter the "SNP position") of the respective figure. In one embodiment, the nucleic acid molecule of the present invention comprises at least about 20 contiguous nucleotides adjacent to the respective SNP position. In one embodiment, the oligonucleotide molecule of the present invention consists of not more than about 100 nucleotides. In one embodiment, the oligonucleotide molecule of the present invention consists of not more than about 50 nucleotides. In one embodiment, the SNP position of the nucleotide molecule of the present invention near or at the center of the molecule; alternatively, the SNP position is at the 3'-end of the oligonucleotide molecule.

Also provided herein is an array of nucleic acid molecules, comprising the isolated oligonucleotide molecule of the present invention, supported on a substrate. The substrate may be any suitable medium, known and readily available to one of ordinary skills in the art, and the array may be addressable.

The present invention further provides a kit comprising an isolated oligonucleotide molecule of the present invention, and a suitable container.

In another embodiment, the present invention provides a method for detecting single nucleotide polymorphism (SNP) in a gene listed in Table 1 below in a bovine cell, the method comprising optionally isolating an DNA from the bovine cell, determining the identity of a nucleotide on the gene of the cell at a SNP position identified in Table 1 below, and comparing the identity to the preferred nucleotide identity at a corresponding position in Table 1.

In one embodiment, the bovine cell may be an adult cell, an embryo cell, a sperm, an egg, a fertilized egg, or a zygote. The identity of the nucleotide may be determined by many methods known and readily available to those ordinarily skilled in the art, such as but not limited to sequencing a nucleic acid molecule comprising a suitable portion of the gene of the cell comprising a respective SNP position, or by hybridizing a suitable probe to a nucleic acid preparation from the cell, which probe may be suitably labeled e.g. fluorescently or radioactively.

The nucleic acid molecule may be isolated from the cell via a large variety of methods, known and readily available to an ordinarily skilled artisan, such as amplification by the polymerase chain reaction (PCR) of genomic DNA of the cell, or when appropriate, by RT-PCR of the mRNA of the cell.

In preferred embodiment, both copies of the gene in a diploid genome are genotyped according to the method of the present invention.

The identity of the nucleotide may be determined based on genotypes of the parent of the cell, genotypes of the daughter of the cell, or both, through genetic analysis methods well-known to those skilled in the art.

A method is further provided for determining whether an individual bovine animal is suitable as a gamete donor for natural mating, artificial insemination or in vitro fertilization, the method comprising detecting the SNP according to the above method of the present invention, and excluding as gamete donor an individual which does not have the preferred allele identity at the respective SNP position as described in Table 1.

In one embodiment, the individual is excluded as a gamete donor if the individual, whose genotype is not homozygous of the preferred allele with regard to the respective SNP position.

The present invention additionally provides a method of selecting a bovine embryo for planting in a uterus, the method comprising genotyping the embryo according to the present invention, while preserving the viability of the embryo, and excluding from planting an embryo which does not have the preferred allele identity at the respective SNP position as described in Table 1.

In another embodiment, the present invention further provides a method for selectively breeding cattle using a multiple ovulation and embryo transfer procedure (MOET), the method comprising superovulating a female animal, collecting eggs from said superovulated female, in vitro fertilizing said eggs from a male animal which has at least one preferred allele identity at the respective SNP position as described in Table 1, implanting said fertilized eggs into other females allowing for an embryo to develop.

In another embodiment, the method for selectively breeding cattle using MOET may further comprise a step of genotyping the male animal according to the method of the present invention.

In another embodiment, the method for selectively breeding cattle using MOET may further comprise a step of genotyping the developing embryo, and allowing pregnancy to proceed only if the genotype of the embryo comprises at least one preferred allele identity at the respective SNP position as described in Table 1.

DESCRIPTION OF THE DRAWINGS

FIG. 1 depicts a partial genomic sequence of MAP1B, showing the locations of SNPs 1, 2 and 3 on the MAP1B gene (SEQ ID NO: 1) and the locations of the primers (1F and 1R, corresponding to positions 2859-2876, and positions 3346-3362, respectively) used to amplify the region comprising the SNP sites. The numbering of the sequences is according to that of GenBank Accession No. (Gene ID: 514739, updated on 12 Jul. 2012), incorporated herein by reference in its entirety.

FIG. 2 is the partial genomic sequence of the MAP1B gene (SEQ ID NO: 6) showing the locations of SNPs 4 and 6 on the MAP1B gene and the locations of the primers 2F and 2R (corresponding to positions 51447-51466, and positions 51931-51948, respectively used to amplify the region comprising the SNP sites. The numbering of the sequence is according to that of GenBank Accession No. (Gene ID: 514739, updated on 12 Jul. 2012), incorporated herein by reference in its entirety.

FIG. 3 is the partial genomic sequence of the MAP1B gene (SEQ ID NO: 2) showing the location of SNP 5 on the MAP1B gene and the locations of the primers 3F and 3R (corresponding to positions 86634-86651, and positions 87260-87278, respectively) used to amplify the region comprising the SNP sites. The numbering of the sequence is per that of GenBank Accession No. (Gene ID: 514739), incorporated herein by reference in its entirety.

FIG. 4. is the partial genomic sequence of the PPP1R11 gene (SEQ ID NO: 3) showing the locations of SNPs 1-4 on the PPP1R11 gene and the locations of the primers 1F and 1R (corresponding to positions −102 to −85, and positions 470-489, respectively) used to amplify the region comprising the SNP sites. The numbering of the sequences is according to GenBank Accession No. (Gene ID: 504846), incorporated herein by reference in its entirety.

FIG. 5 is the partial genomic sequence of the DDX4 gene (SEQ ID NO: 5), showing the location of SNP 2 on the DDX4 gene and the locations of the primers 1F and 1R (corresponding to positions 34014-34031, and positions 34398-34417, respectively) used to amplify the region comprising the SNP site. The numbering of the sequences is according to that of GenBank Accession No. (Gene ID: 493725), incorporated herein by reference in its entirety.

FIG. 6 is the partial genomic sequence of the DDX4 (SEQ ID NO: 4) showing the location of SNP 1 on the DDX4 gene and the locations of the primers 2F and 2R (corresponding to positions 61531-61549, and positions 61867-61884, respectively) used to amplify the region comprising the SNP site. The number of the sequences is per that of GenBank Accession No. (Gene ID: 493725), incorporated herein by reference in its entirety.

DETAILED DESCRIPTION OF THE INVENTION

The present inventor has found that the spermatogenesis genes MAP1B, PPP1R11 and DDX4 showed significant associations with SCR. Table 1 below summarizes the SNPs demonstrated to be significantly associated with sire conception rates according to the present invention.

TABLE 1

Genetic markers significantly associated with sire conception rate

| SNP ID | Location/Position | Nucleotide Identity of Preferred Allele | Nucleotide Identity of Polymorph in GenBank |
|---|---|---|---|
| SNP1.MAP1B | Position 3066 of FIG. 1 | A | A |
| SNP3.MAP1B | Position 3323 of FIG. 1 | T | T |
| SNP5.MAP1B | Position 87071 of FIG. 3 | C | C |
| SNP1.PPP1R11 | Position 112 of FIG. 4 | G | T |
| SNP1.DDX4 | Position 61646 of FIG. 6 | A | A |
| SNP2.DDX4 | Position 34239 of FIG. 5 | G | G |

Three SNPs in MAP1B, in low to moderate linkage disequilibrium (LD), were significantly associated with SCR. After correction for multiple testing, only one SNP in intron 5, SNP 5, showed the most significant association with SCR.

The MAP1B gene belongs to the microtubule-associated protein family and is known to affect neuronal development such as axon growth (Tymanskyj et al., 2012), development of dendritic spine and synaptic maturation (Tortosa et al., 2011), and regulation of the interaction between microtubules and actin microfilaments for axonal development (Montenegro-Venegas et al., 2010). Recent reports on the expression of MAP1B in the male reproductive tract in both rat and human (Queiróz et al., 2006) and in testis of fruit fly and mouse (Bonilla and Xu, 2008) suggest important functions of this gene in the regulation of male fertility. The finding by the present inventor, disclosed herein, that the MAP1B gene is associated with SCR, supports the conclusion that MAP1B plays a role in male fertility across a wide range of species.

The present inventor also found that a SNP in the 5'UTR of PPP1R11 was associated with SCR in the bull population examined in this study. This is the first report of association between male fertility in cattle and PPP1R11, which is consistent with previous reports on the roles of this gene in spermatogenesis in mouse and human. For example, the different isoforms of PPP1R11 (also known as TCTEX5) were found to be expressed in most mouse tissues with high expression in testis, epididymis, and in the head and tail regions of spermatozoa (Han et al., 2007). In a subsequent study, it was shown that mutations in the long transcript of PPP1R11 were associated with normal sperm function (Han et al., 2008). The authors concluded that PPP1R11 plays important roles in sperm motility and spermatogenesis. A recent study reported that an isoform of protein phosphatase 1 (PP1γ 2), which has an essential role in spermatogenesis, forms a complex with PPP1R11 in the testis (Cheng et al., 2009). Given that PP1γ 2 is regulated by PPP1R11, these results further support the idea that PPP1R11 has important functions in spermatogenesis.

The spermatogenesis genes investigated in this study were selected from a pool of genes whose expression is highly conserved in testis of both fruit fly and mouse (Bonilla and Xu, 2008). The protein sequence identities between cattle and human and between cattle and fly are 91% and 32%, respectively for MAP1B and 99% and 47%, respectively for PPP1R11. As such, the association of these genes with bull fertility testifies to the usefulness of the comparative genomics approach in selecting candidate male fertility genes.

To further explore involvement of male fertility genes identified in this study in female fertility, we tested the association of the SNPs in MAP1B, with fertilization and embryo survival rates using data from the IVF system. MAP1B genotypes of the cows, from which oocytes were extracted and used for fertilization and embryo culture, were significantly associated with differential fertilization rate and embryo survival rate. Recently, the expression of MAP1B was found to be downregulated in follicular cystic follicles compared to normal follicles, suggesting that alteration in MAP1B expression may be involved in reproduction failure in cattle (Choe et al., 2010). The instant disclosure again demonstrates the significance of both parental genomes to embryonic development and fertility.

Accordingly, the present invention provides nucleic acid-based genetic markers for identifying bovine animals, especially bulls, with superior fertility, specifically, sire conception rate as a measure of male fertility. In general, for use as markers, isolated oligonucleotide or polynucleotide molecules, or isolated nucleic acid fragments, preferably DNA fragments, as used. Such markers will be of at least 10 nucleotides (nt), preferably at least 11, 12, or 15 nt, usually at least 20 nt, often at least 50 nt. Such small DNA fragments are useful as primers for the polymerase chain reaction (PCR), and probes for hybridization screening, etc.

In one embodiment, the isolated nucleic acid molecule comprises not more than 1,500 nt, or not more than 1000 nt, or not more than 900 nt, or not more than 800 nt, or not more than 700 nt, or not more than 600 nt, or not more than 500 nt, or not more than 400 nt, or not more than 300 nt, or not more than 200 nt., or not more than 150 nt., or not more than 100 nt., or not more than 75 nt.

In the context of the present invention, the term "isolated" refers to a nucleic acid molecule purified to some degree from endogenous materials with which the nucleic acid molecule may naturally occur or exist. At the least, the term "isolated" refers to a nucleic acid molecule separated from chromatin or other protein or components of the genomic DNA. Preferably, the isolated oligonucleic acid molecule or polynucleic acid molecule of the present invention comprises a fragment that is shorter than that which is naturally occurring.

In the context of the present invention, the provided sequences also encompass the complementary sequence corresponding to any of the provided polymorphisms. Where appropriate, and in order to provide an unambiguous identification of the specific site of a polymorphism, the numbering of the original nucleic sequences in the GenBank may be used; alternatively, the numbering may simply refer to the specific sequence in the Sequence Listing accompanying this disclosure.

The term primer refers to a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term primer site, or priming site, refers to the area of the target DNA to which a primer hybridizes. The term primer pair means a set of primers including a 5' upstream primer that hybridizes with the 5' end of the DNA sequence to be amplified and a 3', downstream primer that hybridizes with the complement of the 3' end of the sequence to be amplified. One of these two primers is often referred to as the "forward primer," while the other the "reverse primer."

The term "probe" or "hybridization probe" denotes a defined nucleic acid segment (or nucleotide analog segment) which can be used to identify by hybridization a specific polynucleotide sequence present in samples, said nucleic acid segment comprising a nucleotide sequence complementary of the specific polynucleotide sequence to be identified. "Probes" or "hybridization probes" are nucleic acids capable of binding in a base-specific manner to a complementary strand of nucleic acid.

An objective of the present invention is to determine which embodiment of the polymorphisms a specific sample of DNA has. For example, it is desirable to determine whether the nucleotide at a particular position is A or G. An oligonucleotide probe can be used for such purpose. Preferably, the oligonucleotide probe will have a detectable label, and contains an A at the corresponding position. Experimental conditions can be chosen such that if the sample DNA contains an A, they hybridization signal can be detected because the probe hybridizes to the corresponding complementary DNA strand in the sample, while if the sample DNA contains a G, no hybridization signal is detected.

Similarly, PCR primers and conditions can be devised, whereby the oligonucleotide is used as one of the PCR primers, for analyzing nucleic acids for the presence of a specific sequence. These may be direct amplification of the genomic DNA, or RT-PCR amplification of the mRNA transcript of the gene of interest. The use of the polymerase chain reaction is described in Saiki et al. (1985) Science 230:1350-1354. Amplification may be used to determine whether a polymorphism is present, by using a primer that is specific for the polymorphism. Alternatively, various methods are known in the art that utilize oligonucleotide ligation as a means of detecting polymorphisms, for examples see Riley et al (1990) Nucleic Acids Res. 18:2887-2890; and Delahunty et al (1996) Am. J. Hum. Genet. 58:1239-1246. The detection method may also be based on direct DNA sequencing, or hybridization, or a combination thereof. Where large amounts of DNA are available, genomic DNA is used directly. Alternatively, the region of interest is cloned into a suitable vector and grown in sufficient quantity for analysis. The nucleic acid may be amplified by PCR, to provide sufficient amounts for analysis.

Hybridization may be performed in solution, or such hybridization may be performed when either the oligonucleotide probe or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid. For screening purposes, hybridization probes of the polymorphic sequences may be used where both forms are present, either in separate reactions, spatially separated on a solid phase matrix, or labeled such that they can be distinguished from each other.

Hybridization may also be performed with nucleic acid arrays and subarrays such as described in WO 95/11995. The arrays would contain a battery of allele-specific oligonucleotides representing each of the polymorphic sites. One or both polymorphic forms may be present in the array. Usually such an array will include at least 2 different polymorphic sequences, i.e. polymorphisms located at unique positions within the locus, and may include all of the provided polymorphisms. Arrays of interest may further comprise sequences, including polymorphisms, of other genetic sequences, particularly other sequences of interest. The oligonucleotide sequence on the array will usually be at least about 12 nt in length, may be the length of the provided polymorphic sequences, or may extend into the flanking regions to generate fragments of 100 to 200 nt in length. For examples of arrays, see Ramsay (1998) Nat. Biotech. 16:4044; Hacia et al. (1996) Nature Genetics 14:441-447; Lockhart et al. (1996) Nature Biotechnol. 14:1675-1680; and De Risi et al. (1996) Nature Genetics 14:457-460.

The identity of polymorphisms may also be determined using a mismatch detection technique, including but not limited to the RNase protection method using riboprobes (Winter et al., Proc. Natl. Acad. Sci. USA 82:7575, 1985; Meyers et al., Science 230:1242, 1985) and proteins which recognize nucleotide mismatches, such as the E. coli mutS protein (Modrich, P. Ann. Rev. Genet. 25:229-253, 1991). Alternatively, variant alleles can be identified by single strand conformation polymorphism (SSCP) analysis (Orita et al., Genomics 5:874-879, 1989; Humphries et al., in Molecular Diagnosis of Genetic Diseases, R. Elles, ed., pp. 321-340, 1996) or denaturing gradient gel electrophoresis (DGGE) (Wartell et al., Nucl. Acids Res. 18:2699-2706, 1990; Sheffield et al., Proc. Natl. Acad. Sci. USA 86:232-236, 1989).

A polymerase-mediated primer extension method may also be used to identify the polymorphism(s). Several such methods have been described in the patent and scientific literature and include the "Genetic Bit Analysis" method (WO92/15712) and the ligase/polymerase mediated genetic bit analysis (U.S. Pat. No. 5,679,524). Related methods are disclosed in WO91/02087, WO90/09455, WO95/17676, U.S. Pat. Nos. 5,302,509, and 5,945,283. Extended primers containing a polymorphism may be detected by mass spectrometry as described in U.S. Pat. No. 5,605,798. Another primer extension method is allele-specific PCR (Ruao et al., Nucl. Acids Res. 17:8392, 1989; Ruao et al., Nucl. Acids Res. 19, 6877-6882, 1991; WO 93/22456; Turki et al., J. Clin. Invest. 95:1635-1641, 1995). In addition, multiple polymorphic sites may be investigated by simultaneously amplifying multiple regions of the nucleic acid using sets of allele-specific primers as described in Wallace et al. (WO 89/10414).

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2', 4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

It is readily recognized by those ordinarily skilled in the art that in order to maximize the signal to noise ratio, in probe hybridization detection procedure, the polymorphic site should at the center of the probe fragment used, whereby a mismatch has a maximum effect on destabilizing the hybrid molecule; and in a PCR detection procedure, the polymorphic site should be placed at the very 3'-end of the primer, whereby a mismatch has the maximum effect on preventing a chain elongation reaction by the DNA polymerase. The location of nucleotides in a polynucleotide with respect to the center of the polynucleotide are described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center," and so on.

In some embodiments, a composition contains two or more differently labeled oligonucleotides for simultaneously probing the identity of nucleotides or nucleotide pairs at two or more polymorphic sites. It is also contemplated that primer compositions may contain two or more sets of allele-specific primer pairs to allow simultaneous targeting and amplification of two or more regions containing a polymorphic site.

Alternatively, the relevant portion of the gene of the sample of interest may be amplified via PCR and directly sequenced, and the sequence be compared to the wild type sequence shown in the figures. It is readily recognized that, other than those disclosed specifically herein, numerous primers can be devised to achieve the objectives. PCR and sequencing techniques are well known in the art and reagents and equipments are readily available commercially.

Alternatively, an invasive signal amplification assay, as described in e.g. U.S. Pat. No. 5,422,253 and Lyamichev et al., 2000, Biochemistry 39:9523-9532, both incorporated herein by reference in their entirety, may be used for detecting the SNP of interest. This assay takes advantage of enzymes such as the 5' nuclease activity of a DNA polymerase or the gene 6 product from bacteriophage T7 in their ability to cleave polynucleotide molecules by recognizing specific structures instead of specific sequences. A single-stranded target molecule is annealed to a pilot oligonucleotide such that the 5' end of the pilot forms a duplex with the target molecule. If the 3' end of the pilot oligonucleotide does not pair with the target, a 3' arm is formed. When exposed to a cleavage agent such as a DNA polymerase having a 5' nuclease activity or the gene 6 product from bacteriophage T7, the target molecule is cleaved in the 5' region, one nucleotide into the duplex adjacent to the unpaired region of the target. If a cut in a double-stranded molecule is required, the double-stranded molecule is denatured. Because this unpaired 3' arm can be as short as one nucleotide, this assay can be used for detecting a single-nucleotide difference, e.g. in the context of SNP detection. The pilot oligonucleotide is designed such that it pairs perfectly with one allele, but has a 3', single nucleotide mismatch with another allele. Cleavage only occurs if there is a mismatch between the target molecule and the pilot. To achieve signal amplification, the above invasive reaction is modified such that cleavage occurs on the pilot oligonucleotide. Two oligonucleotides are annealed in an adjacent manner to the target molecule. The resulting adjacent duplexes overlaps by at least one nucleotide to create an efficient substrate, called the overlapping substrate, for the 5' nucleases. The 5' end of the downstream oligonucleotide, also called the probe, contains an unpaired region termed the 5' arm (Lyamichev et al., 1993, *Science* 260:778-783.) or flap (Harrington and Lieber, 1994, *EMBO J* 13: 1235-1246) that is not required for the enzyme activity; however, very long arms can inhibit cleavage (Lyamichev et al., 1993, *Science* 260:778-783). Specific cleavage of the probe, termed invasive cleavage (Lyamichev et al., 1999, *Nat. Biotechnol.* 17 292-296; Kwiatkowski et al., 1999, *Mol. Diagn.* 4, 353-364.), occurs at the position defined by the 3' end of the upstream oligonucleotide, which displaces or "invades" the probe. If the overlap between the adjacent oligonucleotides is only one nucleotide, cleavage takes place between the first two base pairs of the probe, thus releasing its 5' arm and one nucleotide of the base paired region (Lyamichev et al., 1999, *Proc. Natl. Acad. Sci. USA.* 96: 6143-6148, and Kaiser et al., 1999, *J Biol. Chem.* 274: 21387-21394). If the upstream oligonucleotide and the probe are present in large molar excess over the target nucleic acid, and invasive cleavage is carried out near the melting temperature of the probe, a cut probe can rapidly dissociate, and an intact probe will anneal to the target more frequently than will a cut probe, thus initiating a new cycle of cleavage. This allows multiple probes to be cut for each target molecule under isothermal conditions, resulting in linear signal amplification with respect to target concentration and time (Lyamichev et al., 1999, *Nat. Biotechnol.* 17: 292-296).

DNA markers have several advantages; segregation is easy to measure and is unambiguous, and DNA markers are co-dominant, i.e., heterozygous and homozygous animals can be distinctively identified. Once a marker system is established selection decisions could be made very easily, since DNA markers can be assayed any time after a blood sample can be collected from the individual infant animal, or even earlier by testing embryos in vitro if very early embryos are collected. The use of marker assisted genetic selection will greatly facilitate and speed up cattle breeding problems. For example, a modification of the multiple ovulation and embryo transfer (MOET) procedure can be used with genetic marker technology. Specifically, females are superovulated, eggs are collected, in vitro fertilized using semen from superior males and implanted into other females allowing for use of the superior genetics of the female (as well as the male) without having to wait for her to give birth to one calf at a time. Developing blastomeres at the 4-8 cell stage may be assayed for presence of the marker, and selection decisions made accordingly.

In one embodiment of the invention an assay is provided for detection of presence of a desirable genotype using the markers.

The term "genotype" as used herein refers to the identity of the alleles present in an individual or a sample. In the context of the present invention a genotype preferably refers to the description of the polymorphic alleles present in an individual or a sample. The term "genotyping" a sample or an individual for a polymorphic marker refers to determining the specific allele or the specific nucleotide carried by an individual at a polymorphic marker.

The present invention is suitable for identifying a bovine, including a young or adult bovine animal, an embryo, a semen sample, an egg, a fertilized egg, or a zygote, or other cell or tissue sample therefrom, to determine whether said bovine possesses the desired genotypes of the present invention, some of which are indicative of improved reproduction traits.

Further provided is a method for genotyping the bovine genes identified in Table 1, comprising determining for the two copies of the gene in a diploid genome present the identity of the nucleotide pair at the relevant SNP position (see below).

One embodiment of a genotyping method of the invention involves examining both copies of the gene, or a fragment thereof, to identify the nucleotide pair at the polymorphic site in the two copies to assign a genotype to the individual. In some embodiments, "examining a gene" may include examining one or more of: DNA containing the gene, mRNA transcripts thereof, or cDNA copies thereof. As will be readily understood by the skilled artisan, the two "copies" of a gene, mRNA or cDNA, or fragment thereof in an individual may be the same allele or may be different alleles. In another embodiment, a genotyping method of the invention comprises determining the identity of the nucleotide pair at the polymorphic site.

The present invention further provides a kit for genotyping a bovine sample, the kit comprising in a container a nucleic acid molecule, as described above, designed for detecting the polymorphism, and optionally at least another component for carrying out such detection. Preferably, a kit comprises at least two oligonucleotides packaged in the same or separate containers. The kit may also contain other components such as hybridization buffer (where the oligonucleotides are to be used as a probe) packaged in a separate container. Alternatively, where the oligonucleotides are to be used to amplify a target region, the kit may contain, preferably packaged in separate containers, a polymerase and a reaction buffer optimized for primer extension mediated by the polymerase, such as PCR.

In one embodiment the present invention provides a breeding method whereby genotyping as described above is conducted on a bovine animal, especially a bull, and based on the results, certain cattle are either selected or dropped out of the breeding program.

Through use of the linked marker loci, procedures termed "marker assisted selection" (MAS) may be used for genetic improvement within a breeding nucleus; or "marker assisted introgression" for transferring useful alleles from a resource population to a breeding nucleus (Soller 1990; Soller 1994).

A method is further provided for determining whether an individual bovine animal is suitable as a gamete donor for natural mating, artificial insemination or in vitro fertilization, the method comprising determining the identity of one or more SNPs according to the present invention using a method of the present invention, and excluding as gamete donor an individual which does not have the preferred allele identity at the respective SNP position as described in Table 1.

Specifically, an individual bovine animal, especially a bull, is excluded as a gamete donor, if its genome does not have at least:

1) adenine (A) at the position of its MAP1B gene corresponding to position 3066 of FIG. 1;
2) thymine (T) at the position of its MAP1B gene corresponding to position 3323 of FIG. 1;
3) cytosine (C) at the position of its MAP1B gene corresponding to position 87071 of FIG. 3;
4) guanine (G) at the position of its PPP1R11 gene corresponding to position 112 of FIG. 4;
5) adenine (A) at the position of its DDX4 gene corresponding to position 61646 of FIG. 6, or
6) G at the position of its DDX4 gene corresponding to position 34239 of FIG. 5.

In one embodiment, the individual is excluded as a gamete donor if the gene type of the individual is not homozygous of the preferred allele with regard to the respective SNP position.

The present invention additionally provides a method of selecting a bovine embryo for planting in a uterus, the method comprising genotyping the embryo according to the present invention, while preserving the viability of the embryo, and excluding from planting an embryo which does not have the preferred allele identity at the respective SNP position as described in Table 1.

In another embodiment, the present invention further provides a method for selectively breeding cattle using a multiple ovulation and embryo transfer procedure (MOET), the method comprising superovulating a female animal, collecting eggs from said superovulated female, in vitro fertilizing said eggs from a male animal which has at least one preferred allele identity at the respective SNP position as described in Table 1 and above, implanting said fertilized eggs into other females allowing for an embryo to develop.

In another embodiment, the method for selectively breeding cattle using MOET may further comprise a step of genotyping the male animal according to the method of the present invention.

In another embodiment, the method for selectively breeding cattle using MOET may further comprise a step of genotyping the developing embryo, and allowing pregnancy to proceed only if the genotype of the embryo comprises at least one preferred allele identity at the respective SNP position as described in Table 1.

The following examples are intended to illustrate preferred embodiments of the invention and should not be interpreted to limit the scope of the invention as defined in the claims.

genotyping, genomic DNA was extracted from semen samples of 268 Holstein bulls (Genex Cooperative/CRI, Shawano, Wis.) using standard phenol/chloroform protocols. One DNA pool was constructed from 20 random semen samples with equal amounts of DNA. The DNA pool was amplified using primers designed in the 22 candidate genes to amplify 5' untranslated regions (UTRs), exons, introns, and 3' UTRs. The PCR products were sequenced, and SNPs were identified by visually inspecting sequence traces. PCR amplification and sequencing were performed as described in Khatib et al. (2008). Table 2 shows the primer sets used to amplify the nine candidate spermatogenesis genes found to be polymorphic in the bull population.

TABLE 2

Primers used to amplify the nine spermatogenic genes

| Gene | Forward Primer | SEQ ID NO: | Reverse Primer | SEQ ID NO: | Product Size |
|---|---|---|---|---|---|
| DCUN1D1 | ATACCCTTAGGCAGTTAG | 7 | AATTGTAAACCCTGAGAC | 5 | 536 |
| DDX4(1) | AAACACGGAACAGAGGGT | 9 | AGGCAGGATTAGCAAGTATG | 10 | 404 |
| DDX4(2) | AACCAAGTGGCTGGGATG | 11 | CAGACTCAAATGCGACAA | 12 | 354 |
| DNA11(1) | CGGTAAGTGAGCAGCATC | 13 | ACTGAAGCCTTTGCCCTA | 14 | 495 |
| DNA11(2) | CCCAGTGCTCCAAATCCT | 15 | ATGGCTCATCTTGTCTTCAGTA | 16 | 413 |
| DAN11(3) | CGTGACTGGGTTTAGGAT | 17 | CTGGTGGCTGCTGTCTAT | 18 | 602 |
| GAPDHS(1) | CCAGGAAACGGCATCACC | 19 | ACACGCAGCAGGGCAACT | 20 | 414 |
| GAPDHS(2) | GTGAAGGCCAGGGACTATGA | 21 | ACATGAACAAGAGGGCTGCT | 22 | 541 |
| GSTM3 | TTCTCTTCCCTGCAAGTCGT | 23 | TGAGAACAGCTGCCATCATC | 24 | 664 |
| MAP1B(1) | CCATTTCCTAAGGCACAG | 25 | TTCCGCCATCTTCCTACA | 26 | 504 |
| MAP1B(2) | CTTATGGTCGTGATTATGAA | 27 | AAGGCTAACACTGCTGGT | 28 | 502 |
| MAP1B(3) | GGCTGTGACATACCTACC | 29 | CAGACCTTCCCTACTTATT | 30 | 645 |
| PPP1R11(1) | CACATTACGGCGGAACTA | 31 | ATCCCAAGCAGTATCACCTA | 32 | 591 |
| PPP1R11(2) | ACCTGTTCTATCTCCTCCCA | 33 | GTCACCTACCCACCTTGC | 34 | 543 |
| SPATA20 | TTGGAGAAGAAACCCACCAG | 35 | CCTCACAAGCAAGGCTAAGG | 36 | 459 |
| UBC | TCGCTCAGTCGTGTCTTAC | 37 | TCAACCAACGCCTAATGT | 38 | 420 |

EXAMPLES

Materials and Methods

Associations of candidate fertility genes examined were carried out in two experiments. In the first part, single nucleotide polymorphisms (SNPs) in the spermatogenesis genes were tested for associations with sire conception rate (SCR) in a large bull population. In the second part, genes found significantly associated with SCR were tested for association with female fertility traits (fertilization and blastocyst rates). Male fertility genes that play roles in female fertility can be used to improve reproductive performance in cattle using genetic information from both males and females in breeding schemes.

Gene Selection, SNP Identification, and Genotyping for Bull Fertility

A total of 58 spermatogenesis genes, with conserved testicular expression from fly to human, were reported in Bonilla and Xu (2008). Of those genes, only 22 were annotated in the bovine genome. For SNP identification and A total of 24 SNPs located in the nine spermatogenic genes were genotyped in the Genex population (268 animals) by MALDI-TOF MS (GeneSeek Inc., Lincoln, Nebr.).

Imputation of SNPs for Validation of Significant SNPs Found in Genex Population in a Larger Bull Population Obtained from the USDA Solely for the purpose of validating the conclusions drawn from the results using the Genex population, and to increase the sample size and improve the statistical power of the study, the 24 SNPs identified in the 9 candidate genes and genotyped in 268 bulls (from here forward, the reference population) were imputed in a total of 1,720 bulls (from here forward, the imputed population) so that a final dataset of 1,988 bulls with genotypic data was generated for subsequent statistical analyses. Bulls in the reference and imputed populations have been previously genotyped with the Illumina BovineSNP50 Bead Chip, and hence shared SNP were used to infer the genotypes of the unshared SNP in the imputed population. Genotypes of the reference (n=268) and the imputed populations (n=1,720) for the 50K SNP Chip were provided by Genex Cooperative/CRI (Shawano, Wis.) and the Animal Improvement Programs Laboratory of the United States Department of Agriculture (AIPL, USDA; Beltsville, Md.), respectively. SNP with minor allele frequencies below 5% were removed. After data editing, 38,265 SNP spanning the entire bovine genome were available in both populations for the imputation process.

Imputation of SNPs was carried out for each candidate gene separately. In each case, a total of 100 SNP on each side of the gene were used to infer the genotypes of the ungenotyped SNP. Imputation was performed using the population-based haplotype clustering algorithm of Scheet and Stephens (2006), which was implemented via the fastPHASE version 1.2 software using the default settings for all parameters (University of Washington TechTransfer Digital Ventures Program, Seattle, Wash.).

Phenotypic Data for Bull Fertility

The 1,988 bulls genotyped with the 50K SNP Chip were evaluated for sire conception rate (SCR), a phenotypic evaluation of bull fertility provided to dairy producers by AIPL-USDA as described in Peñagaricano et al. (2012). Briefly, SCR is the expected difference in conception rate of a sire compared with the mean of all other evaluated sires (Kuhn and Hutchison, 2008; Kuhn et al., 2008).

In this study, SCR values ranged from −10.66% to +6.80%, and the number of breedings per bull ranged from 303 to 111,402. SCR data were obtained from seven consecutive evaluations provided by AIPL-USDA between August 2008 and December 2010. For bulls with multiple evaluations, the most recent SCR evaluation was used in the analysis.

Statistical Analysis for Bull Fertility

The association between each SNP and SCR was evaluated using the following mixed linear model, $$SCR_{ijkl} = \mu + EVAL_j + \beta SNP_k + sire_l + e_{ijkl}$$

where $\mu$ is the general mean, $EVAL_j$ is the fixed effect of the $j^{th}$ AIPL-USDA SCR evaluation (j=1, 2, ..., 7), $SNP_k$ is the number of copies of one allele of the SNP (corresponding to 0, 1 or 2 copies) carried by the $i^{th}$ animal (i=1, 2, ..., 1988), $\beta$ is the regression coefficient for the SNP considered (also known as the allele substitution effect), $sire_l$ represents the random additive genetic effect of the $l^{th}$ sire (l=1, 2, ..., 246) of the $i^{th}$ animal, and $e_{ijkl}$, represents the random residual for each observation. To detect possible deviations from the additive model, associations between genotype and SCR were evaluated using SNP as a categorical variable.

Random effects were assumed to follow the multivariate normal distribution, $$\left( \begin{array}{c} s \\ \varepsilon \end{array} \Bigg| \sigma_s^2, \sigma_\varepsilon^2 \right) \sim N \left[ 0, \left( \begin{array}{cc} A\sigma_s^2 & 0 \\ 0 & W^{-1}\sigma_\varepsilon^2 \end{array} \right) \right]$$

where s and $\varepsilon$ are the vectors of sire and residual effects, respectively: $\sigma_s^2$ and $\sigma_\varepsilon^2$ are the sire and residual effect variances, respectively; A represents the matrix of additive relationships between sires in the pedigree (1,558×1,558) and W is a diagonal matrix of order 1,988 with its elements representing reliabilities of SCR values. The A matrix was calculated based on a five-generation pedigree of sires downloaded from AIPL-USDA. The association between each SNP and SCR was tested using a likelihood ratio test by comparing to a reduced model without the SNP effect.

Phenotypic and Genotypic Data for Cow Fertility

The most significant SNP for SCR (rs109423562 located in MAP1B) was further investigated for association analysis with fertilization and blastocyst rates—the main cow fertility traits—using an IVF system. The procedures of in vitro fertilization and subsequent embryo culture were described in Khatib et al. (2008). To generate fertilization and blastocyst rate data, a total of 6,282 in vitro fertilizations were performed, and a total of 4,207 embryos were produced using oocytes from 359 ovaries collected from 359 Holstein cows and semen samples from 12 Holstein bulls. For 74 ovaries, oocytes were fertilized by two different bulls each. Fertilization rate was calculated as the number of cleaved embryos at Day 2 post-fertilization divided by the total number of fertilized oocytes collected from one ovary. Blastocyst rate was calculated as the number of embryos that reached the blastocyst stage (Day 8) and appeared normal out of the total number of embryos produced.

The 359 ovaries were genotyped for SNP rs109423562 (G/A) using PCR-RFLP. A 171 bp fragment was amplified using the primers 5'-GCAGCTCTTTTAGGAGTGT-TAGCGTCTGAT-3' (SEQ ID NO: 39) (forward) and 5'-CT-CACAGAGGGCATTTGACA-3' (SEQ ID NO: 40) (reverse). The PCR product was then digested by the restriction enzyme HinfI and electrophoresed on a 2.0% agarose gel. Allele G was cut while allele A was uncut.

Statistical Analysis for Cow Fertility

Association between SNP rs109423562 (G/A) in MAP1B and fertilization and blastocyst rates were analyzed using the following mixed linear model, $$y_{ijk} = \mu + ovary_i + sire_j + SNP_{ijk} + e_{ijk}$$

where $y_{ijk}$ represents the fertilization or blastocyst rate of oocyte k from ovary i fertilized with semen from bull j, $\mu$ represents a general mean for the trait considered, $ovary_i$ represents the random effect of the individual ovary from which oocytes were harvested, $sire_j$ represents the random effect of the sire used in the fertilization, $SNP_{ijk}$ represents the fixed effect of the ovary genotype for the SNP considered, and $e_{ijk}$ represents the residuals, assumed normal, independent and identically distributed with mean 0 an variance $I\sigma_e^2$. Ovaries and bulls were assumed uncorrelated with variance structures $I\sigma_o^2$ and $I\sigma_s^2$, respectively. Association between the SNP and fertilization or blastocyst rate was tested again using a likelihood ratio test by comparing with a reduced model without the SNP effect. All the statistical analyses were performed using the pedigreemm package (Vazquez et al. 2010) of the R language/environment (R Development Core Team 2009).

Results

SNP Identification and Association of Candidate Genes with SCR

Sequencing analysis revealed 24 SNPs in 9 spermatogenesis genes (DCUN1D1, DNAI1, DDX4, GAPDHS, GSTM3, MAP1B, PPP1R11, SPATA20 and UBC) in the bull population using the pooled DNA sequencing approach. All 24 SNPs located in 9 candidate genes were tested for association with sire conception rate first in Genex population and then in a larger population of 1,988 bulls for validation.

Association Analysis in Genex Population

SNPs in the genes MAP1B, PPP1R11, and DDX4 are associated with SCR

For MAP1B gene, a SNP C/T in intron 5 at position 9331992 (University of Maryland bovine version 3.1; UMD3.1) showed significant association with sire conception rate. Primers used to amplify the gene and SNP location are shown in FIG. 1. Frequency of allele T was 25% and frequency of allele C was 75%. The allele substitution effect was −0.15±0.01 (p-value=0.01) so that allele C is favorable for SCR.

For PPP1R11, one SNP (T/G) in in the 5'UTR region at position 28710268 (UMD3.1) was significantly associated with SCR in the Genex population, with allele G associated with increased SCR. SEQ ID NO:6 shows SNP location and primers used to identify the SNP.

For DDX4, two SNPs located at positions 23382814 (SNP1; A/G) and 23410221 (SNP2; G/A) were identified in the gene. For SNP locations see FIG. 3. The two SNPs were in almost complete linkage disequilibrium, so they have the same allele frequencies in the bull population examined. Genotype AA of SNP1 has 0.783 units of SCR versus −0.214 SCR units for GG genotype (P-value=0.05). Similarly, GG genotype of SNP2 has 0.749 units of SCR versus −0.494 for AA genotype.

Association of Spermatogenesis Genes in the Combined Genex and USDA Populations

Three SNPs located in MAP1B and one SNP in PPP1R11 showed significant associations with SCR (Table 3). The SNP with the most significant association with SCR is SNP5.MAP1B located in intron 5 with an allele substitution effect of −0.24 and a P-value of 0.001. The other two significant SNPs were SNP1.MAP1B and SNP3.MAP1B, both located in intron 1 with an allele substitution effect of 0.15 and P-values of 0.025 and 0.039, respectively. After Bonferroni correction for multiple testing, only SNP5.MAP1B remained significant (P-value=0.024). Pairwise linkage disequilibrium (LD) tests of MAP1B SNPs showed a moderate LD ($r^2$=0.38) between SNP1.MAP1B and SNP3.MAP1B and SNP5.MAP1B. The LD between SNP3.MAP1B and SNP5.MAP1B was relatively low ($r^2$=0.14).

SNP1.PPP1R11 located in the 5'UTR region of PPP1R11 showed significant association with SCR with an allele substitution effect of 0.15 and a P-value of 0.046.

TABLE 3

Genetic markers significantly associated with sire conception rate

| SNP ID | Gene | Genotype (N) | Allele substitution effect ± SE | P-value |
|---|---|---|---|---|
| SNP1.MAP1B | M4P1B | GG (463) GA (987) AA (538) | 0.15 ± 0.01 | 0.025 |
| SNP3.MAP1B | M4P1B | CC (972) CT (847) TT (169) | 0.15 ± 0.01 | 0.039 |
| SNP5.MAP1B | MAP1B | CC (1081) TC (763) TT (144) | −0.24 ± 0.01 | 0.001 |
| SNP1.PPP1R11 | PPP1R11 | TT (1033) TG (821) GG (134) | 0.15 ± 0.01 | 0.046 |

Association of MAP1B with Fertilization Rate and Embryo Survival Rate

SNP5.MAP1B located in intron 5 of MAP1B showed the most significant association with sire conception rate in the bull population analyzed above. To characterize its impact on female fertility, we tested the association of this SNP with fertilization rate and blastocyst rate in the IVF system. SNP5.MAP1B showed significant associations with both fertilization rate (P-value=0.027) and blastocyst rate (P-value=0.029) (Table 4). Oocytes collected from genotype CT cows showed the lowest fertilization rate (59.9%) compared with that from CC (66.4%) and TT (66.3%) cows (Table 4). For blastocyst rate, the CT genotype again showed the lowest rate (27.1%) while homozygous CC and TT individuals showed blastocyst rates of 31.0% and 41.8%, respectively (Table 4).

TABLE 4

Association between SNP5 of MAP1B gene and fertilization rate and blastocyst rate

| | Fertilization rate | | Blastocyst rate | |
|---|---|---|---|---|
| Genotype (N) | Estimate ± SE | P-value | Estimate ± SE | P-value |
| CC (321) | 0.664 ± 0.03 | 0.027 | 0.310 ± 0.02 | 0.029 |
| CT (84) | 0.599 ± 0.03 | | 0.271 ± 0.03 | |
| TT (28) | 0.663 ± 0.04 | | 0.418 ± 0.05 | |

REFERENCES

Amann, R. P., J. M. Dejarnette. 2012. Impact of genomic selection of AI dairy sires on their likely utilization and methods to estimate fertility: A paradigm shift. Theriogenology 77:795-817.

Barton, S. C., M. A. Surani, and M. L. Norris. 1984. Role of paternal and maternal genomes in mouse development. Nature. 311:374-376.

Bonilla, E., and E. Y. Xu. 2008. Identification and characterization of novel mammalian spermatogenic genes conserved from fly to human. Mol. Hum. Reprod. 14:137-142.

Cheng, L., S. Pilder, A. C. Nairn, S. Ramdas, and S. Vijayaraghavan. 2009. PPlgamma2 and PPP1R11 are parts of a multimeric complex in developing testicular germ cells in which their steady state levels are reciprocally related. PLoS One. 4:e4861.

Choe, C., Y. W. Cho, C. W. Kim, D. S. Son, J. Han, and D. Kang. 2010. Identification of differentially expressed genes in bovine follicular cystic ovaries. Korean J. Physiol. Pharmacol. 14:265-272.

Dobson, H., R. Smith, M. Royal, Ch. Knight, and I. Sheldon. 2007. The high-producing dairy cow and its reproductive performance. Reprod Domest Anim. 42 Suppl 2:17-23.

Druet, T., S. Fritz, E. Sellem, B. Basso, O. Gérard, L. Salas-Cortes, P. Humblot, X. Druart, and A. Eggen. 2009. Estimation of genetic parameters and genome scan for 15 semen characteristics traits of Holstein bulls. J. Anim. Breed. Genet. 126:269-277.

Feugang, J. M., A. Kaya, G. P. Page, L. Chen, T. Mehta, K. Hirani, L. Nazareth, E. Topper, R. Gibbs, and E. Memili. 2009. Two-stage genome-wide association study identifies integrin beta 5 as having potential role in bull fertility. BMC Genomics. 10:176.

Han, Y. B., H. L. Feng, C. K. Cheung, P. M. Lam, C. C. Wang, and C. J. Haines. 2007. Expression of a novel T-complex testis expressed 5 (Tctex5) in mouse testis, epididymis, and spermatozoa. Mol. Reprod. Dev. 74:1132-1140.

Han, Y., X. X. Song, H. L. Feng, C. K. Cheung, P. M. Lam, C. C. Wang, and C. J. Haines. 2008. Mutations of t-complex testis expressed gene 5 transcripts in the testis of sterile t-haplotype mutant mouse. Asian J Androl. 10:219-226.

Imumorin, I. G., E. H. Kim, Y. M. Lee, D. J. De Koning, J. A. van Arendonk, M. De Donato, J. F. Taylor, and J. J.

Kim. 2011. Genome Scan for Parent-of-Origin QTL Effects on Bovine Growth and Carcass Traits. Front. Genet. 2:44.

Khatib, H., R. L. Monson, W. Huang, R. Khatib, V. Schutzkus, H. Khateeb, and J. J. Parrish. 2010. Short communication: Validation of in vitro fertility genes in a Holstein bull population. J. Dairy. Sci. 93:2244-2249.

Khatib, H., W. Huang, X. Wang, A. H. Tran, A. B. Bindrim, V. Schutzkus, R. L. Monson, and B. S. Yandell. 2009. Single gene and gene interaction effects on fertilization and embryonic survival rates in cattle. J. Dairy Sci. 92:2238-2247.

Khatib, H., R. L. Monson, V. Schutzkus, D. M. Kohl, G. J. M. Rosa, and J. J. Rutledge. 2008. Mutations in the STAT5A gene are associated with embryonic survival and milk composition in cattle. J. Dairy Sci. 91:784-793.

Kuhn, M. T., and J. L. Hutchison. 2008. Prediction of dairy bull fertility from field data: use of multiple services and identification and utilization of factors affecting bull fertility. J. Dairy Sci. 91:2481-2492.

Kuhn, M. T., J. L. Hutchison, and H. D. Norman. 2008. Modeling nuisance variables for prediction of service sire fertility. J. Dairy Sci. 91:2823-2835.

Magee, D. A., D. P. Berry, E. W. Berkowicz, K. M. Sikora, D. J. Howard, M. P. Mullen, R. D. Evans, C. Spillane, and D. E. MacHugh. 2011. Single nucleotide polymorphisms within the bovine DLK1-DIO3 imprinted domain are associated with economically important production traits in cattle. J. Hered. 102:94-101.

Magee, D. A., K. M. Sikora, E. W. Berkowicz, D. P. Berry, D. J. Howard, M. P. Mullen, R. D. Evans, C. Spillane, and D. E. MacHugh. 2010. DNA sequence polymorphisms in a panel of eight candidate bovine imprinted genes and their association with performance traits in Irish Holstein-Friesian cattle. BMC Genet. 11:93.

Memili, E., and N. L. First. 2000. Zygotic and embryonic gene expression in cow: A review of timing and mechanisms of early gene expression as compared with other species. Zygote. 8:87-96.

Montenegro-Venegas, C., E. Tortosa, S. Rosso, D. Peretti, F. Bollati, M. Bisbal, I. Jausoro, J. Avila, A. Cáceres, and C. Gonzalez-Billault. 2010. MAP1B regulates axonal development by modulating Rho-GTPase Rac activity. Mol. Biol. Cell. 21:3518-3528.

Peñagaricano, F., K. A. Weigel, and K. Khatib. 2012. Genome-wide association study identifies candidate markers for bull fertility in Holstein dairy cattle. Anim. Genet. (In press).

Queiróz, D. B., A. M. Silva, G. Gutiérrez-Ospina, C. S. Porto, G. Grossman, P. Petrusz, and M. C. Avellar. 2006. Cells positive for microtubule-associated protein 1B (MAP 1B) are present along rat and human efferent ductules and epididymis. Cell Tissue Res. 325:125-133.

R Development Core Team. 2009. R: A Language and Environment for Statistical Computing. R Foundation for Statistical Computing, Vienna, Austria.

Santos, J. E. P., W. W. Thatcher, R. C. Chebel, R. L. A. Cerri, and K. N. Galvao. 2004. The effect of embryonic death rates in cattle on the efficacy of estrus synchronization programs. Anim. Reprod. Sci. 83:513-535.

Scheet, P., and M. Stephens. 2006. A fast and flexible statistical model for large-scale population genotype data: Applications to inferring missing genotypes and haplotypic phase. Am. J. Hum. Genet. 78:629-644.

Shook G. E. 2006. Major advances in determining appropriate selection goals. J. Dairy Sci. 89:1349-1361.

Telford, N. A., A. J. Watson, and G. A. Schultz. 1990. Transition from maternal to embryonic control in early mammalian development: A comparison of several species. Mol. Reprod. Dev. 26:90-100.

Tortosa, E., C. Montenegro-Venegas, M. Benoist, S. Härtel, C. Gonzalez-Billault, J. A. Esteban, and J. Avila. 2011. Microtubule-associated protein 1B (MAP1B) is required for dendritic spine development and synaptic maturation. J. Biol. Chem. 286:40638-40648.

Tymanskyj, S. R., T. M. Scales, and P. R. Gordon-Weeks. 2012. MAP1B enhances microtubule assembly rates and axon extension rates in developing neurons. Mol. Cell Neurosci. 49:110-119.

Vazquez, A. I., D. M. Bates, G. J. M. Rosa, D. Gianola, and K. A. Weigel. 2010. Technical Note: An R package for fitting generalized linear mixed models in animal breeding. J. Anim. Sci. 88:497-504.

Weigel, K. A. 2006. Prospects for improving reproductive performance through genetic selection. Anim. Reprod. Sci. 96: 323-330.

What is claimed is:

1. A method for implanting an embryo comprising:
in vitro fertilizing cattle eggs to obtain fertilized eggs, culturing fertilized eggs into developing embryos
detecting the identity of a nucleotide of a MAP1B gene of an embryo at a position corresponding to position 1986 of SEQ ID NO: 1, wherein the MAP1B gene comprises the nucleotide sequence of SEQ ID NO: 1, and identifying an embryo that has an adenine at said position, and
implanting said identified embryo into a suitable female bovine.

2. The method of claim 1, wherein the identity of both copies of the gene in the embryo is determined.

3. A method according to claim 1, wherein the nucleotide is detected by sequencing the gene or a relevant fragment thereof.

4. A method according to claim 3, wherein the gene or a relevant fragment thereof is isolated from the animal's nucleic acid sample via amplification by a polymerase chain reaction.

5. A method of selecting a bull bovine animal as a breeder, the method comprising:

obtaining a sample of the animal's nucleic acid, wherein the nucleic acid comprises at least a partial MAP1B gene comprising SEQ ID NO: 1,
detecting an adenine nucleotide at a position of the MAP1B gene of the animal corresponding to position 1986 of SEQ ID NO: 1,
selecting the bull bovine animal that has an adenine at said position, and
using bovine cell or tissue from the selected bull animal in a breeding procedure.

6. The method according to claim 5, wherein the bovine cell or tissue is sperm.

7. A method according to claim 5, wherein the nucleotide is detected by sequencing the MAP1B gene or a relevant fragment thereof.

8. A method according to claim 7, wherein the gene or a relevant fragment thereof is isolated from the animal's nucleic acid sample via amplification by a polymerase chain reaction.

9. The method of claim 5, wherein the identity of both copies of the gene in the bovine bull animal is determined.

* * * * *

SEQUENCE LISTING

```
<160> NUMBER OF SEQ ID NOS: 40

<210> SEQ ID NO 1
<211> LENGTH: 3780
<212> TYPE: DNA
<213> ORGANISM: Bos taurus
<220> FEATURE:
<221> NAME/KEY: misc_feature
<222> LOCATION: (1986)..(1986)
<223> OTHER INFORMATION: r is a or g
<220> FEATURE:
<221> NAME/KEY: misc_feature
<222> LOCATION: (2081)..(2081)
<223> OTHER INFORMATION: r is g or a
<220> FEATURE:
<221> NAME/KEY: misc_feature
<222> LOCATION: (2243)..(2243)
<223> OTHER INFORMATION: y is t or c

<400> SEQUENCE: 1
gagcgcgctc tgcagaggcc gaatagcggt tcgctgggaa accctgggcg gggccgtaag    60
```

```
ggtccagcgg gcgcagactc gggcgcgcgg accgacccgc cccgcagccc caccgggct    120 gccgcagtgc ccccgcccga tgcacctgcc ccccacactg cggcgccccc actgggcgcg   180
gccggccggg cgtgcgttcc gccggtgctt ggggtgctg tgcgccctct cgtctgcctc    240
aacccggctt tgttgcgctc gaagtccccg ggtgggcagc tctgtcctct gcctttccct   300
ttccccccgg catcgcagac ctcccccttct ccctgaccga ggtcgcgggt ccctccacaa  360
ccccagcccg cgctctattc tctcggggtg gtgctgaagc gcgtctgccc cgagacaccg   420
gctggtgggc gtggtgcagt ccgcactgcg gtctctacgg cagcccgagg cggacaaagg   480
gcgttcacgc agccctcgtt ccccacgccc gcccccact ccccatgaaa gacgcgagaa    540
aaccttgttt tagatgaaaa aaaattaaac tctagtggtc tgcctctgca tttgaaaacg   600
gtcgcctgtg cccagaacaa aaggctgcag ggtggagact cgagttgcag acctggttct   660
tttgtttaac tttaaagcac tggtgttact ttttggctta aaaaagaaa aaaatgtgag    720 cagaaagcag acttgttatt ttattcggaa aaaaaaatg gaagaatagg ctaggtcaat    780
agtgaaatgc ctcatttgag catctaataa cccttcattt gtcaaactat agtcctttga   840
atttgatcag tactaattta gtttatttgc acatttctc cttggaaaat tcacacgta    900 ctgactttgg gtgtggctgc tgtatgaatc tatgactttg gattttaaa aaaatattat    960 ttgtcagcac ttttgctggg aagtaataat aaagcaggtg tgtttctatg tataaaaggt  1020
gcataagcac ccgatgtggt gtgaggagag ggaccctcat ccccattttg gagatggggg  1080
cccagagggg caggaaggat agggagacca gctcaaggtc acaccactca taagtgacag  1140
aatgccggct ctgcagcatc actggttttt ggcccgtcat gatgttagtg caggccaggc  1200
gaacatcaca ggaagatcaa agagcaattt ctagagcttg cctttataca aaggcagtag  1260
tcatccactt gtgggcagca ccccatgcag ggaggtggct cagcaatcac cttccatgta  1320
attatcttcc tgctttgtta ctctgctgat cacccttta gtgccctatt tctcaggggg   1380
tttattgaag ctgcttctgt ttgaggataa actagattca cccaagttat cggtcactgt  1440
gacgtggtct cgactatttt tcacgctact ggaacttagt gatcgagttc aattttgtct  1500 tcttgccccct tttcttttt aaaatttatt gatgtattat gtagtgaggg aaaggctcaa   1560
atcataaacg aggagcttgg tgaattttca caaaaagaca tacctgatcc cgatcaagaa  1620
acggacattc ctgggacccc cagaaaccct ctcaggtgtc ctttctcagtc agcatgcctt  1680 cctgattttt tagtgccctg atttagtcag cttttttgcgg ggaactctga aatagcagta  1740
ttgatcccat taagaatcaa ccaagtgaat gagcaaagcc atttcctaag gcacagtaac  1800
agatgctgct tttcctctgg agatcaactc tcttgggtcc tggggtcttg gatgcagctc  1860
aaaccacagg gccttccagt gctaagggga aatactgctc ctgtagcttt tctgacagag  1920
atgacttagc aacagggcag gctggctgtt gccctggcct gatatgatgc ttcctcagct  1980
ctcagrttcc agcagggcct cctcctccag aggtcactct gataccatgg ctgcggtggc  2040
tggtgcccat gggaccagtt gtgtgaagca agatggagat rctccggggg ctcggccctg  2100
cttgtgtgcc gcagccttc cgcagggaaa gcggttcatc ttctgcccct cttgcttgtc   2160
tcccctctca tccggatgag gctctctgag tctgagacc ctaggacttt ggattttgc    2220 catttgatga tttaaggctc tayggggaaac ctagaaaata aatctgtagg aagatggcgg  2280
aaatgcaagt acatcaatag gcctgaatca gcccaccatg gaggctgagt acatgcttct  2340
tgaaacctag tgttactgaa tcaaactgag gcagctcacc tgcatgcagt aaagccaatt  2400
```

```
tactgacccc aggttgtggt gaaggaaagt gcagcattat tgtaagatgc tgatgtaagg    2460
agaacgggga gctcgtgctt aagaccccca aaatccccca agggtttcag caaagcattt    2520
ttaaaggcag tgtaagggag ggtgtcccag agtgtgtgat cagctcatgc accattctct    2580
aattgagaat tagattgatg atgaggtaac aagactacgt tgggcttcct tgctggctta    2640
gatggtaaag aatctgccta caatgcagga gagctcggtt tgatccctgg gttgagatcc    2700
cttgaagaag ggcatgacaa cacattccag tattcttgcc tggaaaatcc ccatggacag    2760
aggagcctgg tgggtacagt ccatggggtt gcaaagagtt ggacatgact gagtgactag    2820
gcacagcaca agactatgtt aatgaggact atgtgcggat ggtcatcaag tagttaattt    2880
cttccatttg atggtgattt tagcatctga aaaataactc aggaaatata cttcagatac    2940
taatatctag gtatttcaga gaggaactaa agcagagggt ataggggagg ggtctgtccc    3000
aggaatgtcc cataaggtcc tgcttggtta cacaaggaca gaagaccatc attcgtttct    3060
tcagcttcat tcaaaatgca taatgtaggg tctggtcatt tcttaagtct gaaacaacag    3120
tctttgctca gactggtcta gctttattta gttagttatg caggactcca tgccaaacca    3180
ttgtcactcc ttggcacctc ctttgccccc ttcctaatta gtctccaaca tagacttaac    3240
agtcatcccc gttttagca gagtctcccc tcctccagtt tattttggga tgtagactac    3300
atacactcat gttttgcaaa acgaattcta gagccttgtg aaaagttttc attgcttcgt    3360
tttattttat tttttaaact aaaacatgta aaaaacacta agtgtcagtt tggtttcact    3420
tgctgttaga gtgtaacttt cctctggtta acattgggaa tcagcaggat ttgttcatca    3480
gaaagataga tgtgtgtaac atctactgcc ctggattttt agatgtaagt tttgctaatt    3540
acattgtcat ttattgaata ctttcagtct acattggtta agagaattaa gaacccagga    3600
aagagttagg gctttgtttc cattttgttt taacaggaaa acaacggggt gatgggaatg    3660
aaaagaaatg ttgaggaatg atatatttac tatatccatc catcttcata cgtttcaaaa    3720
tcaaaaggca gatggatttc tgcttgcgct gcttaattgg tattatctac tcaaagagtt    3780
```

<210> SEQ ID NO 2
<211> LENGTH: 3900
<212> TYPE: DNA
<213> ORGANISM: Bos taurus
<220> FEATURE:
<221> NAME/KEY: misc_feature
<222> LOCATION: (1991)..(1991)
<223> OTHER INFORMATION: y is c or t

<400> SEQUENCE: 2

```
agtgctctgg ttaatcaacc agtgaggtca gctgaccact gggtacccag tacagattga     60
gaaaagagca tccaagactc tacttattcc attctgacca cactgcctca ctaatacaga    120
ctcaacatct tgttttaggt cgaaattcag cttggcaaga gcaagcatcc ctgacttcat    180
gttcttagac ttatcaagtt ctcggcagtg atctgggttt tgatgaatc tgggtttctg     240 atgatccagc ttcattttgt tgcttcaaaa caatcacagg gatttgaatt catatatttt    300
atttgcttta catagttact tgaaggtttt agatcacagt tcacaaacat gtaaagcaaa    360
aaataagcaa cactttcttg atttattatg gaaaaattca gtatttagta ctttaggaag    420
tactagttac aggtacaagt ttttactttt aggcaacgtg aagcagcaat ttcaagactc    480
atatcagatt tcctctttt atttgcacat agaaaacaaa ctgaatttgt tcatgcttag    540
aatttgtata gagccaccag ataataaatc ttgatctaaa ggacttaaca gtgaccatgc    600
acttaggaga aaacatgaaa tcaattcaaa cagataaaaa cccaactgaa atttgctgcc    660
```

```
aaactcatga aacttacact atagcccaca caattgattt tatcactttt ttttttttg      720 gtcatttaaa gataattttg agggaaagtg agttaatttg aatttacatt gaggatgctt      780
tcccaacaga ttttttaaa agacaaaact gcactattaa ttaattttaa aacaaacctg      840
ggtcaacttc cagtggttct atcagtttgg gcttctatga gcaatgttca tttggtgtca      900
acgggagtga ttcaaggtgc aagtggaaac tgcaggcatt taaaaatatt agatgatctg      960
taactcacaa acctctgcta caagtcagaa ttctttggga gatttacaca tgaatatgtt     1020
taggactttt agcttaggtt cattataatg gctggttaat ctattcatga aatgattcag     1080
tttatccaaa taccagtttg gctgattctt actacccct gccctccaaa ataaaaataa      1140
accagttcat agctgatttt gactgtggga tggcagtctc tatacatccc atggagaaag     1200
gcaagagaat taaatttagg ggatcttgct agtattttaa gtggtttcac agcagtggtc     1260
tcaaaccaga tacacattag cattggctgg gatgctttta aaagtgatg gtaccctggt      1320 cagtgaagcc ttaccatagc cattgaagcc agggcatctg tattaagcat gctaagtgat     1380
tctaatcatg tggccaggag gaagaaccac tgccttacaa tgctagttct gttaatgttt     1440
caaccttctg attagaacaa atcagaaagc caattctaga aacaaggtag ccagaaactg     1500
agattaatct gaaccttcat tttgcccagg ctttctgact tgggggaat tttggctgtg      1560 acatacctac cccttacctc agtccggtat gttctgattg gctagagaaa gcagagtctt     1620
tctgaacctt cctgttgcta aagtttggta tctagtcttg tctaaggaga gacgtctacc     1680
atttagagga ctgtcctaag gagagaatac agtgttttca tcagtttatg catgaggctg     1740
aggtgctgag ggtcttggag atcatatgac attaagatct gactactggc tagatcaaat     1800
gtgaggggat aatattcagc tgtgggccaa actgcttta aatgaaatcc taacatgaat      1860
tactaagatg gcttaactat gctttaccaa atgcagatgc tttcctttgt cctttaaaat     1920
ctatttctta gatcacattt caaattaaaa gacacactag cagctctttt aggagtgtta     1980
gcgtctagtt ytatctttgg ggaaagcctt ggcaactctt cttaattgct aatgtgttta     2040
agggaaacgc cccattcttc atttctcctg agatggtaaa cagtcaagtg atgctgtctc     2100
agactgccag tgtcaaatgc cctctgtgag agagggagt gccaacaccc actcccatgt      2160
cccagagcgc cttctgggga ataagtaggg aaggtctgct ggacagatga gtctctttgc     2220 attttttgtga ccctggcctt ctctttgttt ttatttgttt acaaagggcc aggaaccacc    2280
aagacgtcca agccctcagc tgtgccccca ggcccccctg tgtacctgga cctatgctat     2340
attcccaacc atagcaatag taagaatgtc gacgttgaat tttcaagag agtgagatcg      2400 tcctactacg tggtgagtgg gaacgaccct gctgctgagg agcccagccg ggctgtcttg     2460
gatgccttgc tggaagggaa agcccagtgg ggcagcaaca tgcaggtaag agttccagga     2520
cggtgtttgc acaacacgtg gagctgtgtc cagaggcagc aggaagggat cgtgtttaat     2580
gaggcaccac cgtggatccc catgaggtgc ccacagggcc tgctgcactt ggacaaagtg     2640
gatttcacac acacaagctg gtctaaaagc attcgcgcca ccagccacca tggacttgga     2700
ggaaggccac tttaccaccc taagtataa tctgcagagt gggcccaaga ttacacaccg      2760
ttcatatacc aagaaaatta accagcgtaa ccaagtgtca tatttccatg tgagatggat     2820
aaagattagc cttacttgt ctttcccaag tagacaaaag ctagagatat ggccatttag      2880
aaaatcagct gtccacatga gattctgcag gagcactgct gaaaatggtc ctcagcagga     2940
cactcccaac acccaaacat cgtaatgagc cacaaaccac tcattatttc agttatggat     3000
```

```
tttatctaag ttttacttac ggttttgtat agtgatctag taaactgtat ttgcataacg    3060
ttaaatagaa atcctggtta tttcattata tgaaatctaa tgcactcagt ggcctcttac    3120
tgaatactag gtagaattta agctagtaat cacttaccca ccccactcct ctgtcccaa     3180 acacacacac aaagacataa atctttgctc tcatgatgaa atgttagtta acatgcaatt    3240
agaaggtttt cggctgcatt aataactaaa gccccttgt tttaaatatg caatatcttt     3300
aatgtaaaac atcagttgtg ttaaagaaaa tacaagaaat tccaccttaa ctgaagaact    3360
tctcataatg ctaaagaatt gaaaactgat atagatgaac taactggcta gtcatgactt    3420
gcttttggtt ctagtcttca actgccccag aaaaactaat ttttagcag ctttattctg     3480 gttcctagaa aatgtaagtt ggaaagtcct atggattttc taaggacaat agaatatttt    3540
tctctttccc tttcttttc taatggtcta attaatacct tactgctgtt ctattttcc     3600 ccaccccatt tctggttctg ctcttcagta gctgttttct ctctccctgc aggtgacct    3660 gatcccgact catgactcag aagtgatgag ggaatggtac caggagaccc atgagaaaca    3720
gcaggacctc aacatcatgg ttttagcaag cagcagcaca gtggttatgc aagatgaatc    3780
cttccctgca tgcaagatcg aactgtaaca accaaggtca gccgcaccac aggatttgaa    3840 cttgtttcc agaaattctt cgatttgaaa ccaccttttc taaaaaaaaa gtcaattcat    3900
```

<210> SEQ ID NO 3
<211> LENGTH: 3060
<212> TYPE: DNA
<213> ORGANISM: Bos taurus
<220> FEATURE:
<221> NAME/KEY: misc_feature
<222> LOCATION: (232)..(232)
<223> OTHER INFORMATION: k is t or g
<220> FEATURE:
<221> NAME/KEY: misc_feature
<222> LOCATION: (1332)..(1332)
<223> OTHER INFORMATION: w is a or t
<220> FEATURE:
<221> NAME/KEY: misc_feature
<222> LOCATION: (1606)..(1606)
<223> OTHER INFORMATION: m is a or c
<220> FEATURE:
<221> NAME/KEY: misc_feature
<222> LOCATION: (1659)..(1659)
<223> OTHER INFORMATION: y is c or t

<400> SEQUENCE: 3

```
gcggcgcctg cgcactgtca cattacggcg gaactaatcc ggcgacccag cgctttgacg      60
catttagtac caggaaggga aaaggggggac cacagaacgc gtcacacccg gaagtaggga    120
gccggaactg ggttggaca ggttatcccc aggggtgggg cagcggaggc ccaggaggag     180
ggggaaaaaa gaaggtggag gatcctggct gctaatctga atcgataccg aktctcttag    240
acctcagaga cacagaaaag acagaagggt gcctcatccc ctttcctccg cttctctctc    300
tcctcagcct tagccatggc ggaggcaggg gccgggctga gtgagaccgt cactgagaca    360
acggttaccg tgacaacgga gcccgtgaga aaggctgggg gcggtgctgt ttaggggtct    420
gagagatacc gggagggaag ggataaggct ttggagagtt gctggatggg ctgggcctgg    480
ggatatggga ggaagtgggt ttgggagaat cgcagagtat tagggatttt ttggtgtgtc    540
agagttggtg cagaaggctg gtcaagtgac atgcaataga gttaagatgt aggtgatact    600
gcttgggatg gtggtgtctg taagtattga aagactggga acttggcgat taatgagcaa    660
gggatgtact gggggaaatg aagggttgtg tgagaaagca tggttggaag ctcgctgtag    720
ggaaacttga cactaagcat gcttatcaat aaatatttct tgaagagatt attgcaaacg    780
```

```
gaagcagagg gaatgaggga acaagaaaag ggagatgatg ggagtatttt gaaaaatcag    840
agatgtagag aaaaacagcg tttttgcaaa aacattgctt tcaataggag atgttcctgt    900
cgggcttaat aacccttttga ttaagggagt ttagagtaat agttactaga gatgccagga   960
tgctggagaa taggtggata acagattggg agggctgggc ttgaggatga gagatgtgag   1020
aacagagtca tttctttaat gggaaaaaga ataggcgttc tgggaaaaga aagggagatc   1080
aaagtttagg cattggtgac tgaaaaaata attttcatgt attaatacca ccaaagatga   1140 tttgggagg aagatggagg aacagcgagg attatatttt cctttgaaga tttgctggga    1200
ctttccctag gttaggaatt gtatcttctc tgtatactag tggttactaa gaatactaag   1260
aacagaattc ctcaagggac tccttgaggt caaaaacctg ttctatctcc tcccagcatc   1320
agctcctctg twgctgtgtt tgtgatcctg attgaactgg gaaagggaag aaaggaggcc   1380
ccagggagga cgcaggaaga gttagtagga ggggactagc taggtatgcc tatccttctt   1440
aaccttccag gagaaccgga gcctaaccat caaacttcgg aaacggaagc cagagaaaaa   1500
ggtggaatgg acgagtgaca ctgtggacaa tgaacacatg ggccgccgct catcaaaatg   1560
tgagtaattg ttgccccaca gtaacgctgg agtcctggct cccctmagca tatcttttgc   1620
cttcaggcat tcactggcct tcccaaagcc cccagatgyt cacagtcctg tggctgcctt   1680
ggtggttctc tgttatcagg gagaggaggt taaagttaga gggaaagagg tagggagggg   1740
cttcaatttc catgtgcaag gcctaaagtc aaaggtatct gaggtgggag aagaggagct   1800
ttggattccc ggctggaaag gcaaggtggg taggtgacag agtcccagag tgtaggcctg   1860
gggaagctgg atctggaagg tagaaggaga aaatggtggg aagtaggaat tttgactgag   1920
atccagtggg aatggaactg acactacatc tgaactcttc ctccttttc actgggctcc    1980 tccatccaaa tccaggctgc tgtatttatg agaaacctcg ggcctttggc gagagctcca   2040
cagagagtga tgacgaggaa gaggagggct gtggtcacac acactgtgtg cggggccacc   2100
gcaaaggacg gcgtcatgca acccccggga caagccccac cagccctccc cagcctcctg   2160
acccctccca gccccctcca gggccaatgc agcactaaat tcctcgctcc cccaccattc   2220
ctgtgtctgt ctggccctga atgtattcat gtggctactc ggggactaaa cccacgattt   2280
gatcccttct ccagccccct cctccctct cctctgcctg acagagggaa gagggagagg    2340
aaggtggaca gagatcctgg aattctgact tgctgctatt ccagaaccta ggcttctggg   2400 ttccccagc cctcatttct ccttacaata cccagcctcc tctctccagg gatccaggca    2460
tcttgatccc aatctttttc ctttgttctc actgccaaac tgcctgtcct gggatccagt   2520
tatcttggcc ccttgcactc tctacttgag ttccaaacag ctaaattggg tttccagcag   2580
ccccagcttt cactgccagg gtcctagtca gattccaggc aatcttgctc cagctatgct   2640
tgttaatcct ggcttagagc tcttccactt atgtatttat gtcatcctaa ctcttagtcg   2700
ttgcctgtgg gatgtgaggt cttctgtgag acctcagggc tcctagccct ttcccttctc   2760
tcctgcccac ttcccccaag cccttaagag gagttaggag agagggaggt ctttgtcctt   2820
ctcaccttta atgagaaatg gaaaaaagaa atgggcatgt cctctctcct caccgttctc   2880
atgtgactag ggtttctgac aaaactggct ccaagactag tcacttagag cccactatct   2940
cctcagcctt tggtcttcca acttaggaga cagatccgac ccaggggcct gggtccctgg   3000
gagaggatga aaagggagg gagccaagag atgcaatctc ccccttcct tccaaggcct     3060
```

<210> SEQ ID NO 4

<211> LENGTH: 4080
<212> TYPE: DNA
<213> ORGANISM: Bos taurus
<220> FEATURE:
<221> NAME/KEY: misc_feature
<222> LOCATION: (2006)..(2006)
<223> OTHER INFORMATION: r is a or g

<400> SEQUENCE: 4

```
ctgatatctg agattaaata tcacctctaa aaccttcctt ttttgcagtc ctactatctt      60
acttaggaaa ttccattcag tatcttgccg ggagaattcc agggacagag gtgcctggtg     120
ggctatagtc catggggtca caaagaatca atcggacatg actgagcgac tgacactcat     180
tccagttgtt cagacacaaa aatatgaggc atctttgatt tctttctcca gtgtacatat     240
ctgatctgtc agcagagtcc tcttgtttct gtctagcatc aaactatatc agaacccatc     300
agttgctaag ttaaaacaaa gatcagatct acttcttgcc tccaaaccca atggcttccc     360
tcctcaaagt aaagatcttt cagtggattt caaggcactt catgaaatgg cttccatcat     420
ccctctccaa atcctgctgc tctccattgc ttaccctatt ctagctgcac tttgctcatt     480
actcatcccc acacgtacca gacatggttc tacctcattg cctttgttct tgatattccc     540
tctgcctaga acgtaaaaac cagatgggga cctcttttct ggtttgtttg tttgtttgtg     600
agcacgtaaa gaacacctat acctagaac ctttatattt gttcttacct ctgacctata     660
atattgtttc ttcagatatc tgaatagttc acttgtttag taatatctgt cctcagatgt     720
catctaatta gagaaggtgc ataaacccat ttggcccttt attctgctaa atttttttct     780
tttttagact taatgcatca tatttgttat ttacctctcc acaatgagtg cagatgcttt     840
gttttatttg ctgtgttttc agtatctaga atagatactg gcatctactg ggtgctaaat     900
gtttgttaat aaatggagac agctgatagg gacatggagg agtgggatta caaaaagtaa     960
caccctgtta cttctattca ggctatagat tattatcttt cctctctaac attttataga    1020
aaatttcttg gtgtggaaga gtctttggct catgcttata tttaaaccaa ttaacaaagc    1080
taacaagtaa atattcttta atgtgttaag accctgagat aatatcttat atatctatat    1140
atataagata ctttggggat taagggtttt gaattgagat aatgttgaaa catagaatat    1200
tgtagagttt gtcagccctg ggttgaatgc tattattatg aatgcctctg gcagtcaagg    1260
taaaataata gattctataa ccatgggaag aacaaaggaa tttatttata gagagggaaa    1320
tgaagggctg gagccaaatt tggaactgct aagagttggc aggtagatat catttatctt    1380
tccctaagtc tctacttatt ggttggccta tgaaggcaag gggcaagcgg tcgtttttct    1440
tttttttag tcataaagta ggaaaaagtc cttgtctctc tatctttgac atttatccac    1500
tcaggaaata tttgaattgc tcttacctat caggcctgag tttaggtgct gggaatacag    1560
tggtgaataa gacagtttcc tactcaccct atgcttttt ttcttttcct aattttgtag    1620
tttgaatgtt tcattgtctt gtaggtgatg aagaactat ggtctttgtt gaaactaaga    1680
aaaaagcaga ttttattgcc acttttcttt gtcaagaaaa aatatcaaca acaagtattc    1740
atgggtgagt agattattat gatttcctag taaggaggta acttctattt gtcatttgtt    1800
aagaaatgtt ggtatattta actagtaaaa aatcctggaa ttaggatctc aagatctagc    1860
tattattctt catctttaag ttttataag aaccaagtgg ctgggatgga tgagttagaa    1920
gtatcttaag ttcctcatca tgattatcaa gcagtctcac ttagtctctc taatccttag    1980
atctaggtgc ttattcagct aatctrtcca gtgcttggta ttttttttcac tgggcctcaa    2040
aaatgtcata gtaacacaac ttcattggca ctttactagg agatctaaaa tattaattgg    2100
```

```
tgaatatgta gaattccgag attatacttt taaaaaatca ggaattttg agaaaggatt      2160 tgatcaacta gttgtgtatt ttttgtcaaa actagaaaca gtttattagt tggtaagatt      2220
tgatgtttgt cgcatttgag tctgtatttt ggctgtaggt attagctgtc accttcatct      2280
gcaaatggag ttaattgtcc taacctcaaa gtattattgt gagaattaaa tgatgactta      2340
caagaaatta gtataatact ttgtatgtaa gaagtagaca ttaatgttaa ctgttgctat      2400
ttttgtttta ctgttatcca ttgaacttat ccaaaaagaa atctatccat tgaactttaa      2460
tggttgtctt taatagtttt cttaagggct attctaatac atgctttgtt ttctttcaag      2520
tgatcgtgaa cagagagaaa gagagcaagc tcttggagat ttccgctgtg aaagtgccc       2580 tgttcttgtt gctacttcag tagctgcccg agggctggat attgaaaatg ttcagcatgt      2640
tattaatttt gatcttcctt ctaccattga tgaatatgtt catcgaattg ggcgtactgg      2700
tcgttgtgga aatactggca gagctatttc cttttttgat ctggaatcag atagccagtt      2760
agcacagcct ctagtgaaag tgctatcaga tgtaagtttt taattttaa aactgaatgg       2820 atagtgttct taccttgtca ttgaaagcag acattttata tgtatggatt ttcagttcag      2880
ttcatttgct cagtcgtgtc tgactctttg caaccccatg gactgcagta tgccaggctt      2940
ccctgtccat caccaactcc cagagcttac tcgaactcat gtccatcgag ttggtgatgc      3000
catccaaccg tctcatcttc tgtcatcccc ttctcctcct gccttcaatc tttgccagca      3060
tcagggtctt ttccaatgag tcagttcttt gcatcaggtg gccagagtat tggagcttca     3120
gcttcagcat cagtccttgc gatgaatatt caggactgat ttcctttagg gttgactggt      3180
ttgatctcct tgtagtccag gagactcaag agtcttctcc aacatcacag ttcaaaagca     3240
tcaattcttc agcactcagt tttctttgaa gtccacttct cacatccata catgactact      3300
gaagaaacca tagctttgac cagacagacc tttggtggca aaataatgtc tctggttttt      3360
aatatgctgt ctaggttggt catagctttt ctgcttttct tccaaggagc aagcatcttt      3420
taatttcatg gctgtagtca ccatctgtag tgatttcgga gccccaaaa ataaagtctc       3480 tcactgtttc cattgtttct ccatctgttt gccctgaatt gatgggaccg gatgccatga      3540
tcttagtttt ctgaatgttg agctttaagc caactttttc actctcttct ttcactttca      3600
tcaagaggct ctttagttct tcgctttctg ccataagggt ggtgtcgtct gcgtatctca      3660
ggttattgat atttctccag gcagtcttga ttctaccttg tgcttcatcc agcccagcat      3720
ttcacatgat gtactctaaa atcccacggg cggaggagcc tggtaggctg cagtccatgg      3780
ggtcgctaag agtcggacac gactgagtga cttcactttc actttcact ttcatgcatt       3840 tgaggaggaa atggcaaccc actccagtgt tcttgcctgg agaatcccag ggacggggga     3900
gcctggtggg ctgccgtcta tggggttgca cagagtcgga cacgactcaa gcgacttagc     3960
agcagcagca tataaattaa ataagcaggg tgacaatata cggccttgac atactccttt      4020
ccctatttgg aaccagtctg ttgttccatg tccagttcta actgttgctt cttgatctgc      4080
```

<210> SEQ ID NO 5
<211> LENGTH: 3900
<212> TYPE: DNA
<213> ORGANISM: Bos taurus
<220> FEATURE:
<221> NAME/KEY: misc_feature
<222> LOCATION: (2139)..(2139)
<223> OTHER INFORMATION: r is g or a

<400> SEQUENCE: 5

```
gagtgaggcc ctggatcctg tatttaaaag cctccctgct gactctgatg cctctttcat    60
ttggtaacca ctgatctatg gagtctttat aacttctctg cacacagatg tatagtgtat   120
tttgtggtta ttttcccgt atcttgtgtc cctagctgg tccagtatag taataaggag     180
ctcagatttt ggaatcagac acccgggatt gagacccag atccttctct tcctgtcagt    240
tgtattattt taaaaagca tgtttaactt tgtatttctt tttctgtt tataaattga      300
ggataatacc cacctcataa ggttttgtg aggatttaaa aagttaaaat agaattcatt    360
tagaagagtg tcagatggat actgttttat gtgttattat tacattattt ttctataatt   420
agtagattat aactgatctt gggatcatta tctcatttt gtttgtgctt aactttattt    480
ttaactctac agagattatt ttttaataac tttttatttt gaaatcattt gactcaagaa   540
gtttcaaaaa tagtacagaa gatttccttc agcttgcctc taatgtaatt gtactcctca   600
cccagtttct cctaatgtca ttagcctatt ttaattccca gtgtggtcaa ataactgta    660
agtttgtttg aggagaacag ttggccaaag gttatgtgag gtgggttttc tttcatatat   720
gacaataaat gttagctacc atcatcatta ttccagatga tgatgaatta ttatatcatc   780
aaataataat tccattattc cagattattc taagaatctt tgcagaattc tttctttcct   840
cttcaacccc cttgtatgaa atctttgctt ctgagaaggt tgtcttgatg ttaaatgatt   900
ctttaggaat attgtcaatt gttgatgtca gctcaaatag gagcctgcaa caagagctgt   960
gggtcattgt ttattataaa tcaatattaa ttgagtagat tagtactttt gtacataaac  1020
aactgatagc ttttaatctg tcgagccaca tatgtcatca ctgggaccta gttctctggc  1080
actaaatgtt agtgatatgt acaaagattc cttgaaacca tcttggtatt ttccaaatat  1140
gggtttattg gaatcttcta gaaagcttaa agttattact gaaagttata tcaataaggt  1200
ataattttt aatttagaaa aattgttcat tcctggatat cactctgcac attcaaaatg   1260
aatctctcta gggtgggttc tgataattta ttttaacca actttcctga taattttag    1320
tcatccttca gtgtagtgat cctcatacta ctatgtataa actctggtaa tgttacttaa  1380
taatgtcact aaggacagaa agccgggatg tccccaaatg cttccattag gatggatagg  1440
gaaaagtttg catatattaa aaaaacacta taatgcctca ggtttattaa gaaagacaat  1500
ttacagatta atgatgacat tataaataca atagttatgc atttctgaga tccgtttgac  1560
tactcaactg ttcagatatt tctgaaactg tttcgtgaca tttatgaaat tcttattttt  1620
tggctgtgct cagaacttga cagataacat gcttaacatt tagtatttag gtatattagg  1680
tgattttaa aaagaattga ctgaataatg tgtttgtatt ttgttgttat ggtgatttta   1740
aaatttaaaa ttttgttcat atgttagctt atgaatatat tttttctcag taatttctct  1800
tgtgatagta ctatttagat actacagtaa tataaatact gcaataatta tttagatgct  1860
attcacatgt taaattttta ttcaagaatc tagtattgac tgtgaagata atcaaacacg  1920
gaacagaggg ttttccaaga gaggcggtaa ggaccatgtt ttggaacaac ttgtacttaa  1980
gacagaaatt aaactgaaaa attgattttg gaagagctga agaaaaatt ctggtggtga   2040
aaacctttca agaaaaatac tttggcatat cctttatgct gttaatattt gagttaatat  2100
tcagtaggtg tctctccttc tgctttctga tgtcactcra tttgtctttt cctaagacct  2160
ccagagtgtt ctatgaacta caaaaggtgg gactgtgtga atcttggtca ttcacagtat  2220
agataaactg ggatgtcttt gtctctgagt aggaacattg gagatatggg ggaagggaga  2280
agttgtagat taattaccat acttgctaat cctgcctctg cttgaggtga gatggtataa  2340
aaattatagt gctcagttct ggattatcta taggcagaca tgttaaaata gcaacaatat  2400
```

```
ccacgaaaaa ccacagtgaa cttataaaat tgctacaagt gtgcaaatat atttatgata    2460
gaactttagt gtttggagct gcactagata catcatagtt tttgctgcaa cttggagata    2520
tcgttttccc ttgcctatta gatgattggc tcattgaata gatcattgaa tagcaggcct    2580
tcctagtgaa gctgagactt gctgtggatt tcactatagc cttggatgag ttgtgagggg    2640
cggtgggtag gaatttggtg gtgaatcagt tcagtcgctc agttgtgtct gactcttttgc   2700 gacccccatga attgcagcat gccaggcctc cctgtccatc accgactcct ggagttcatt    2760
caaactcaag tccatcgagt cggtgatgcc atccaaccat ctcatcctct gttgtcccct    2820
tctcctcctg cccccaatcc ctcccagcat cacagtcttt tccaatgagt cagctcttcg    2880
catgaggtgg ccaaagtact ggagtttcag ctttagcatc attccttcca agaacaccc    2940 aggactgatc tcctttagaa tggactagtt ggatctcctt gcagtccaag ggactctcaa    3000
gagtcttttc caacaccaca gttcaaaagc atcaattctt cggcgctcag cttttcttcac   3060 agtccaactc tcacatccat atatgaccac tggaaaaacc atagccttga ctatatggac    3120 cttttgttggc aaagtaatgt ctctgctttt cagtatgcta tctaggttgg tcataacttt    3180
ccttccaagg agtaagcgtc ttttaatttc acagctgcag tcaccatctg cagtgatttt    3240
ggagcccaga aaaataaagt ctgccactgt ttccactgtt tccccatcta tttcccatga    3300
agtgatggga ccagatgcca tgatctttgt tttctgaatg ttgagcttta agccaacttt    3360
ttcactctcc tctttcactt tcatcaagag gcttttagt tcctcttcac tttctgcata    3420
agctgagtct ttaatggcaa ttgtagggggg ccctgcaatg atggggcgga catttagtta    3480
agaaatagac tcgtctttta acattgctct ccttcccct ttaacaagga gttttgacac    3540
taatgttcct aaaacatagc tcttttggtt ttctgcagaa cagtggctat cttttcttact    3600 attcagttttt ctttaaatca ttttaattca tatttaagtg cagcaatgaa aagccagttg    3660
cagctctttg tgcttgatcc tgacttattg actagtgtag gttgtctagt agggtgtccc    3720
tgattgctat tttctttaga tgtatacatt tgaaggtaga aaacttgtgt gtgacacggt    3780
ggtcactcag taaatacaga tgtgtgtgta aatagaacct tatctaagtt tatgttgaag    3840
tatcatgtca tacaggaaca ggttggtgca tatgtcataa atgtatacag ctcagtgatt    3900
```

<210> SEQ ID NO 6
<211> LENGTH: 3720
<212> TYPE: DNA
<213> ORGANISM: Bos taurus
<220> FEATURE:
<221> NAME/KEY: misc_feature
<222> LOCATION: (1981)..(1981)
<223> OTHER INFORMATION: r is g or a
<220> FEATURE:
<221> NAME/KEY: misc_feature
<222> LOCATION: (2097)..(2097)
<223> OTHER INFORMATION: y is c or t

<400> SEQUENCE: 6

```
tccagcctgt tctgtggatg tttgaacttg agaagtgggg tctttgtcca gaggaaacac      60 tgctttttcgc ctggtagagg atgggctcca tccgaatcat acccagtttg ttcctttgct    120
acttcttcat cttcccgtgg tttcatgtcg agtcagaatg taaggactgt ttagcttttg    180
tgaggggcaa aaatgtgttt ttgaactgga caaggtaagg tttgaaccca ttcttttgtc    240
tttcttgtat acttccattt tcactttgag cacaaagcag gttggggaag caggagggg    300 gaagatgtta ttgtggatta gagacagagg aaaaggcagg tggggggttg gaactgaacc   360
```

-continued

```
ccacttcctg cagccgtttc ccagccggtt ttgaaaagac tctgaaagga gaataacgtc    420
tttaatcaag agcaatagta ttagctcctt tactataagt aatacttttc tttgagccta    480
tatttatttt accgggctag aaatagctga agttattcca gcagccatga ctattgtcta    540
ggagttggat gtgggctggc aatagactgg ctgattacac tgtttagaaa taaacccctt    600
tgttggcagt ctcttctggt gagaatggtt cataaaggtc cctgtggctg gttgttccat    660
ggtgcttgct tttatatcag ttcagtaccc tcataatgag gtggtcttct agaatatatt    720
attataactc tgttgcagag ggcgtagggc tcgtcagtta tgcaggcaac atcacaaagc    780
tttggaagaa atctcttaat taagtgctag ggctggtgct gcagtgaagg gatgaatgga    840
ctgaaatgct tccatctctg agcgtctttt caaactaaac gggccctttg ccgcatcata    900
gccaggagtc cagcagacgg acacactgag aaagtggtgg tggatgtgat tggtgatgtt    960
cctgacttcc tctgacctac ccctggggat ttctgtactt cacgtcacac gtggctcctt   1020
gttgatggta tggtgaaaac ataggtgttg aaagaaccag aattgacagc agttcagcga   1080
ccttttgggt cttcaggtct gagaccatac cctaggcagc atcagtccct ccacggtaga   1140
tggcactgga cttctgtgg cgtttaagac ctaacgttct gtgactgaga atgtggcctg   1200
tcttggccac agctggtacg atgacaagat gactatctga gttaggaaga aaaagtgaag   1260
tgaaagtcat ttagttgtgt ccgactccgt gacctgcagc tcttctaggc tcctctaggc   1320
tcctctgtcc acgggatttt ccaggcaaga ataatggagt gggttgccat ttcctcctcc   1380
agatcttccc aacccaggtc tcctgctttg caggcagatt cgttatgtgt ctacaatgaa   1440
agaaagggta ggagcaaata cagaggcaga agtttgttcc ctcctaggaa ggttattctt   1500
gatctggcca ttcaaagacc ttttcatttc ctctcagatc ttttcaaagt gactaacctg   1560
aaaaatcttt gatgtgtggg ccaggacatg atggaggaag gcatctttt ctttcctttt   1620 actccttgga gaagagatga aactaaaagg gctctaaggg aaaaaaaaa attcttaaaa   1680 aaaaaagtt aataaaaaaa caaaaggtaa taaatagctc tttgtaaaca gcttaccacc   1740
ttacttcctg tggttacatg cattacctta tggtcgtgat tatgaaagat ttctagagaa   1800
acgttaggat gatcacataa ctccctccta aggcgccagt ggagcccaaa gtctttgctg   1860
ttcacgtgcc ttgtgagtgg cccaacacag tggggacttt ataaatatca aatcattgtc   1920
gttaaaaaac acttcccgct tcactctgag acccttcctt ttaaggagtg catgtggtgg   1980
rggaggatta atgacagcac agcgagtgtg gcttgaaggt ggtgacatca cccggcttga   2040
acccttcagt gccgggtgag aggattttca tctcatccat cctcctgagt ttgccaygag   2100
gggtctccaa gaacaggaaa agaggagtct gaggagagga gacttctgga cattctgtga   2160
tagtcccctg gctctgtgcc gtattgtttt gtaaataagg cagttatggt ttctagtctg   2220
ttgtttttct acaaaaatgg aggacgtgtg accagcagtg ttagccttcg tgaatgagat   2280
tctgtgtttc ggccatcact ggttcaagta ggtaacctaa gagctgagct taagttgctt   2340
ctcttgcagc ccatctttgg cttcagtaa ggaatctgag caacattaga ctgagaatca   2400
gacaccttta ccatcacttt acgggatgct tccatttgct gtgtgatagg acgcaggtgc   2460 aggagggag cgtctggacc ccagagtcgt ggcgtcagga ggtcccgtgg gagcatcctc   2520
agcctctgca gtggtcctac caggagagga aggtgcttgg gtgtcgggat acccatgctc   2580
aactcctggt tctcccgtta tcatgccctg tgactctgga caagtcactt agcctctctg   2640
aaccttaatg tttgtatctg ttaagacaag ggtttggaat agatccgtcc aaattcacat   2700
ttctgcagac ctgggttact ggctgtaggg ctctaattgg actggatctc ctcatccctg   2760
```

-continued

```
ataacctatt tccagggcgt ggggcccccct gctgtacagc gtcttgcttc attttcccac    2820
cgtcttttag ctcccatctg gatgccatct tctgtgtagt atggaagcct tcctaaacca    2880
tccagtgact cccttgagcc cttcctctcc ctgctgaggt gtgtgtccag gagccagggg    2940
ccatcctgcc cttttttgctg gccactgccc catggttctg gtctcatgcc agggtcggca   3000
ctctgtcagg atgtggtggg ttgagtttat acctgatctt gatgtaaaca catggcctct    3060
gcccagtcat ttgttcctgt tcccacactg gcttccagct cttttgtgga ctctgactct    3120
ctgctctcct ggcctcctga tggctggaca tcttttcttt tccttctaga atgccacccc    3180 ttttttttgtt gtctaacttg taaaagcccc atagatcatc tcccatttca aacccttaga    3240
gatgactatc ttgatatgtt gataagaggt gaactttctc agaggagttt cttgttacag    3300
tgtcaaatgt ggttataaat cactggaact taaggatctg tctgccaagc agtagacacg    3360
agtttgatcc ctgggtcagg aagatccgct gaagaaggga atggctatcc atgccagtat    3420
tcttgcctgg agaatcccat ggacagagga acctggaggc tacagtctat ggtgtcacca    3480
aaaaattgga catgacttag tgactaaaca acaacaataa gagaagcttt aagggaggtc    3540
agccctctct ccaccccagc actagaacag tccctagagc agagtctccc aaatctgcct    3600
ggtgagcaga atcatcaccc agtgctttta ttattatttt aatatttatt aaaaaatttt    3660
ttttgtttgg ctatattagg tcttagttgt ggcatgaggg atctttagtt gcaacatgtg    3720
```

```
<210> SEQ ID NO 7
<211> LENGTH: 18
<212> TYPE: DNA
<213> ORGANISM: Artificial Sequence
<220> FEATURE:
<223> OTHER INFORMATION: Forward Primer DCUN1D1

<400> SEQUENCE: 7 ataccctttag gcagttag                                                  18

<210> SEQ ID NO 8
<211> LENGTH: 18
<212> TYPE: DNA
<213> ORGANISM: Artificial Sequence
<220> FEATURE:
<223> OTHER INFORMATION: Reverse Primer DCUN1D1

<400> SEQUENCE: 8
aattgtaaac cctgagac                                                   18

<210> SEQ ID NO 9
<211> LENGTH: 18
<212> TYPE: DNA
<213> ORGANISM: Artificial Sequence
<220> FEATURE:
<223> OTHER INFORMATION: Forward Primer DDX4(1)

<400> SEQUENCE: 9
aaacacggaa cagagggt                                                   18

<210> SEQ ID NO 10
<211> LENGTH: 20
<212> TYPE: DNA
<213> ORGANISM: Artificial Sequence
<220> FEATURE:
<223> OTHER INFORMATION: Reverse Primer DDX4(1)

<400> SEQUENCE: 10
```
aggcaggatt agcaagtatg                                                    20

<210> SEQ ID NO 11
<211> LENGTH: 18
<212> TYPE: DNA
<213> ORGANISM: Artificial Sequence
<220> FEATURE:
<223> OTHER INFORMATION: Forward Primer DDX4(2)

<400> SEQUENCE: 11
aaccaagtgg ctgggatg                                                      18

<210> SEQ ID NO 12
<211> LENGTH: 18
<212> TYPE: DNA
<213> ORGANISM: Artificial Sequence
<220> FEATURE:
<223> OTHER INFORMATION: Reverse Primer DDX4(2)

<400> SEQUENCE: 12
cagactcaaa tgcgacaa                                                      18

<210> SEQ ID NO 13
<211> LENGTH: 18
<212> TYPE: DNA
<213> ORGANISM: Artificial Sequence
<220> FEATURE:
<223> OTHER INFORMATION: Forward Primer DNAI1(1)

<400> SEQUENCE: 13
cggtaagtga gcagcatc                                                      18

<210> SEQ ID NO 14
<211> LENGTH: 18
<212> TYPE: DNA
<213> ORGANISM: Artificial Sequence
<220> FEATURE:
<223> OTHER INFORMATION: Reverse Primer DNAI1(1)

<400> SEQUENCE: 14
actgaagcct ttgcccta                                                      18

<210> SEQ ID NO 15
<211> LENGTH: 18
<212> TYPE: DNA
<213> ORGANISM: Artificial Sequence
<220> FEATURE:
<223> OTHER INFORMATION: Forward Primer DNAI1(2)

<400> SEQUENCE: 15
cccagtgctc caaatcct                                                      18

<210> SEQ ID NO 16
<211> LENGTH: 22
<212> TYPE: DNA
<213> ORGANISM: Artificial Sequence
<220> FEATURE:
<223> OTHER INFORMATION: Reverse Primer DNAI1(2)

<400> SEQUENCE: 16
atggctcatc ttgtcttcag ta                                                 22

<210> SEQ ID NO 17
<211> LENGTH: 18
<212> TYPE: DNA
<213> ORGANISM: Artificial Sequence

```
<220> FEATURE:
<223> OTHER INFORMATION: Forward Primer DNAI1(3)

<400> SEQUENCE: 17
cgtgactggg tttaggat                                                 18

<210> SEQ ID NO 18
<211> LENGTH: 18
<212> TYPE: DNA
<213> ORGANISM: Artificial Sequence
<220> FEATURE:
<223> OTHER INFORMATION: Reverse Primer DNAI1(3)

<400> SEQUENCE: 18
ctggtggctg ctgtctat                                                 18

<210> SEQ ID NO 19
<211> LENGTH: 18
<212> TYPE: DNA
<213> ORGANISM: Artificial Sequence
<220> FEATURE:
<223> OTHER INFORMATION: Forward Primer GAPDHS(1)

<400> SEQUENCE: 19
ccaggaaacg gcatcacc                                                 18

<210> SEQ ID NO 20
<211> LENGTH: 18
<212> TYPE: DNA
<213> ORGANISM: Artificial Sequence
<220> FEATURE:
<223> OTHER INFORMATION: Reverse Primer GAPDHS(1)

<400> SEQUENCE: 20
acacgcagca gggcaact                                                 18

<210> SEQ ID NO 21
<211> LENGTH: 20
<212> TYPE: DNA
<213> ORGANISM: Artificial Sequence
<220> FEATURE:
<223> OTHER INFORMATION: Forward Primer GAPDHS(2)

<400> SEQUENCE: 21
gtgaaggcca gggactatga                                               20

<210> SEQ ID NO 22
<211> LENGTH: 20
<212> TYPE: DNA
<213> ORGANISM: Artificial Sequence
<220> FEATURE:
<223> OTHER INFORMATION: Reverse Primer GAPDHS(2)

<400> SEQUENCE: 22
acatgaacaa gagggctgct                                               20

<210> SEQ ID NO 23
<211> LENGTH: 20
<212> TYPE: DNA
<213> ORGANISM: Artificial Sequence
<220> FEATURE:
<223> OTHER INFORMATION: Forward Primer GSTM3

<400> SEQUENCE: 23
ttctcttccc tgcaagtcgt                                               20
```

<210> SEQ ID NO 24
<211> LENGTH: 20
<212> TYPE: DNA
<213> ORGANISM: Artificial Sequence
<220> FEATURE:
<223> OTHER INFORMATION: Reverse Primer GSTM3

<400> SEQUENCE: 24
tgagaacagc tgccatcatc                                               20

<210> SEQ ID NO 25
<211> LENGTH: 18
<212> TYPE: DNA
<213> ORGANISM: Artificial Sequence
<220> FEATURE:
<223> OTHER INFORMATION: Forward Primer MAP1B(1)

<400> SEQUENCE: 25
ccatttccta aggcacag                                                 18

<210> SEQ ID NO 26
<211> LENGTH: 18
<212> TYPE: DNA
<213> ORGANISM: Artificial Sequence
<220> FEATURE:
<223> OTHER INFORMATION: Reverse Primer MAP1B(1)

<400> SEQUENCE: 26
ttccgccatc ttcctaca                                                 18

<210> SEQ ID NO 27
<211> LENGTH: 20
<212> TYPE: DNA
<213> ORGANISM: Artificial Sequence
<220> FEATURE:
<223> OTHER INFORMATION: Forward Primer MAP1B(2)

<400> SEQUENCE: 27
cttatggtcg tgattatgaa                                               20

<210> SEQ ID NO 28
<211> LENGTH: 18
<212> TYPE: DNA
<213> ORGANISM: Artificial Sequence
<220> FEATURE:
<223> OTHER INFORMATION: Reverse Primer MAP1B(2)

<400> SEQUENCE: 28
aaggctaaca ctgctggt                                                 18

<210> SEQ ID NO 29
<211> LENGTH: 18
<212> TYPE: DNA
<213> ORGANISM: Artificial Sequence
<220> FEATURE:
<223> OTHER INFORMATION: Forward Primer MAP1B(3)

<400> SEQUENCE: 29
ggctgtgaca tacctacc                                                 18

<210> SEQ ID NO 30
<211> LENGTH: 19
<212> TYPE: DNA
<213> ORGANISM: Artificial Sequence
<220> FEATURE:
<223> OTHER INFORMATION: Reverse Primer MAP1B(3)

-continued

```
<400> SEQUENCE: 30
cagaccttcc ctacttatt                                                 19

<210> SEQ ID NO 31
<211> LENGTH: 18
<212> TYPE: DNA
<213> ORGANISM: Artificial Sequence
<220> FEATURE:
<223> OTHER INFORMATION: Forward Primer PPP1R11(1)

<400> SEQUENCE: 31
cacattacgg cggaacta                                                  18

<210> SEQ ID NO 32
<211> LENGTH: 20
<212> TYPE: DNA
<213> ORGANISM: Artificial Sequence
<220> FEATURE:
<223> OTHER INFORMATION: Reverse Primer PPP1R11(1)

<400> SEQUENCE: 32
atcccaagca gtatcaccta                                                20

<210> SEQ ID NO 33
<211> LENGTH: 20
<212> TYPE: DNA
<213> ORGANISM: Artificial Sequence
<220> FEATURE:
<223> OTHER INFORMATION: Forward Primer PPP1R11(2)

<400> SEQUENCE: 33
acctgttcta tctcctccca                                                20

<210> SEQ ID NO 34
<211> LENGTH: 18
<212> TYPE: DNA
<213> ORGANISM: Artificial Sequence
<220> FEATURE:
<223> OTHER INFORMATION: Reverse Primer PPP1R11(2)

<400> SEQUENCE: 34
gtcacctacc caccttgc                                                  18

<210> SEQ ID NO 35
<211> LENGTH: 20
<212> TYPE: DNA
<213> ORGANISM: Artificial Sequence
<220> FEATURE:
<223> OTHER INFORMATION: Forward Primer SPATA20

<400> SEQUENCE: 35
ttggagaaga aacccaccag                                                20

<210> SEQ ID NO 36
<211> LENGTH: 20
<212> TYPE: DNA
<213> ORGANISM: Artificial Sequence
<220> FEATURE:
<223> OTHER INFORMATION: Reverse Primer SPATA20

<400> SEQUENCE: 36
cctcacaagc aaggctaagg                                                20

<210> SEQ ID NO 37
```

```
<211> LENGTH: 19
<212> TYPE: DNA
<213> ORGANISM: Artificial Sequence
<220> FEATURE:
<223> OTHER INFORMATION: Forward Primer UBC

<400> SEQUENCE: 37
tcgctcagtc gtgtcttac                                                   19

<210> SEQ ID NO 38
<211> LENGTH: 18
<212> TYPE: DNA
<213> ORGANISM: Artificial Sequence
<220> FEATURE:
<223> OTHER INFORMATION: Reverse Primer UBC

<400> SEQUENCE: 38
tcaaccaacg cctaatgt                                                    18

<210> SEQ ID NO 39
<211> LENGTH: 30
<212> TYPE: DNA
<213> ORGANISM: Artificial Sequence
<220> FEATURE:
<223> OTHER INFORMATION: Forward Primer PCR-RFLP

<400> SEQUENCE: 39
gcagctcttt taggagtgtt agcgtctgat                                       30

<210> SEQ ID NO 40
<211> LENGTH: 20
<212> TYPE: DNA
<213> ORGANISM: Artificial Sequence
<220> FEATURE:
<223> OTHER INFORMATION: Reverse Primer PCR-RFLP

<400> SEQUENCE: 40
ctcacagagg gcatttgaca                                                  20
```